(12) United States Patent
Goto

(10) Patent No.: US 10,420,462 B2
(45) Date of Patent: Sep. 24, 2019

(54) IMAGE PROCESSING APPARATUS THAT GENERATES A TOMOGRAPHIC IMAGE OF A SUBJECT BASED ON PHASE-ADJUSTED MEASUREMENT SIGNALS FROM WHICH A BACKGROUND SIGNAL IS SUBTRACTED, AND RELATED IMAGING APPARATUS, IMAGE PROCESSING METHOD, AND COMPUTER READABLE STORAGE MEDIUM

(71) Applicant: CANON KABUSHIKI KAISHA, Tokyo (JP)

(72) Inventor: Atsushi Goto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 68 days.

(21) Appl. No.: 15/822,662

(22) Filed: Nov. 27, 2017

(65) Prior Publication Data
US 2018/0153395 A1   Jun. 7, 2018

(30) Foreign Application Priority Data
Dec. 1, 2016   (JP) ................. 2016-233723

(51) Int. Cl.
*G06K 9/00* (2006.01)
*A61B 3/10* (2006.01)
(Continued)

(52) U.S. Cl.
CPC ............ *A61B 3/102* (2013.01); *A61B 5/0066* (2013.01); *G01B 9/02083* (2013.01);
(Continued)

(58) Field of Classification Search
CPC .................................................... A61B 3/102
See application file for complete search history.

(56) References Cited

U.S. PATENT DOCUMENTS 9,058,652 B2   6/2015 Hanebuchi et al.
2009/0002713 A1*   1/2009 Ohbayashi ......... G01N 21/4795
356/477
(Continued)

FOREIGN PATENT DOCUMENTS

JP   2013-156229 A   8/2013

OTHER PUBLICATIONS

Anna et al (NPL: "Improvement of the dynamic range using background subtraction in single shot wide-field optical coherence tomography" DOI: 10.1080/09500340.2014.995734, p. 14, Jan. 2015), (Year: 2015).*

(Continued)

*Primary Examiner* — Oneal R Mistry
(74) *Attorney, Agent, or Firm* — Venable LLP

(57) ABSTRACT

An image processing apparatus includes a memory that stores instructions, and at least one processor that executes the instructions to acquire measurement signals including information on a tomography of a subject in a depth direction obtained by performing optical coherence tomography on the subject, to acquire a base signal based on the measurement signals, and to calculate phase shifts between the measurement signals and the base signal. The processor further executes the instructions to smooth the phase shifts, to adjust phases of the measurement signals corresponding to the smoothed phase shifts based on the smoothed phase shifts, and to generate a background signal corresponding to a noise component based on the phase-adjusted measurement signals. In addition, the processor subtracts the background signal from the phase-adjusted measurement signals, and generates a tomographic image of the subject based on the phase-adjusted measurement signals from which the background signal is subtracted.

23 Claims, 8 Drawing Sheets

(51) Int. Cl.
 *G01B 9/02* (2006.01)
 *A61B 5/00* (2006.01)
(52) U.S. Cl.
 CPC ............... *G01B 9/02091* (2013.01); *G06T 2207/10101* (2013.01); *G06T 2207/30041* (2013.01)

(56) References Cited

U.S. PATENT DOCUMENTS

2011/0090459 A1* 4/2011 Rathjen .................. A61B 3/107
 351/212
2014/0028997 A1* 1/2014 Cable ................ G01B 9/02091
 356/51

OTHER PUBLICATIONS

De Boer, J.F., "Spectral/Fourier Domain Optical Coherence Tomography", Drexler W,. Fujimoto J.G. (eds) Optical Coherence Tomography, 2008, pp. 147-175.
Moon, Sucbei, et al., "Reference spectrum extraction and fixed-pattern noise removal in optical coherence tomography", Optics Express, Nov. 22, 2010, pp. 24395-24404, vol. 18, No. 23.

\* cited by examiner

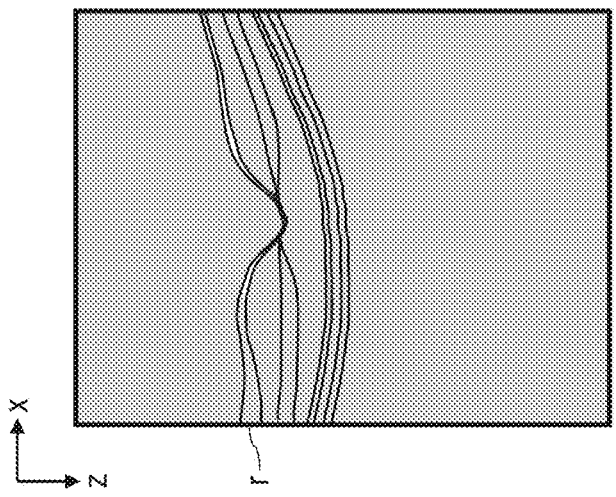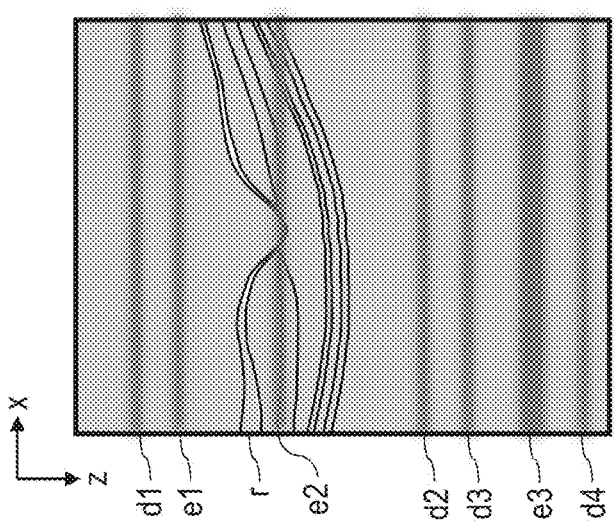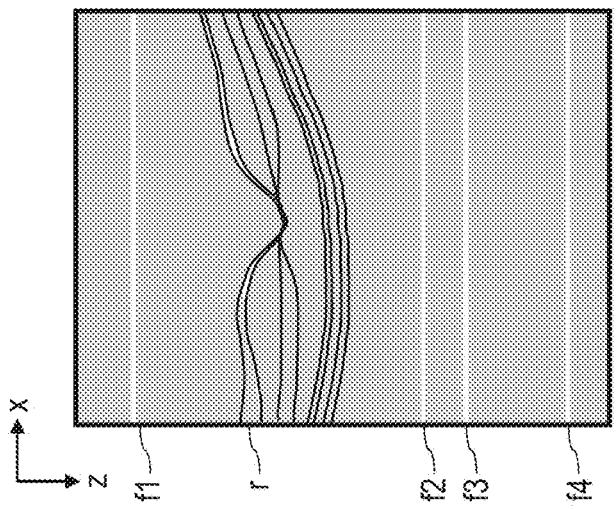

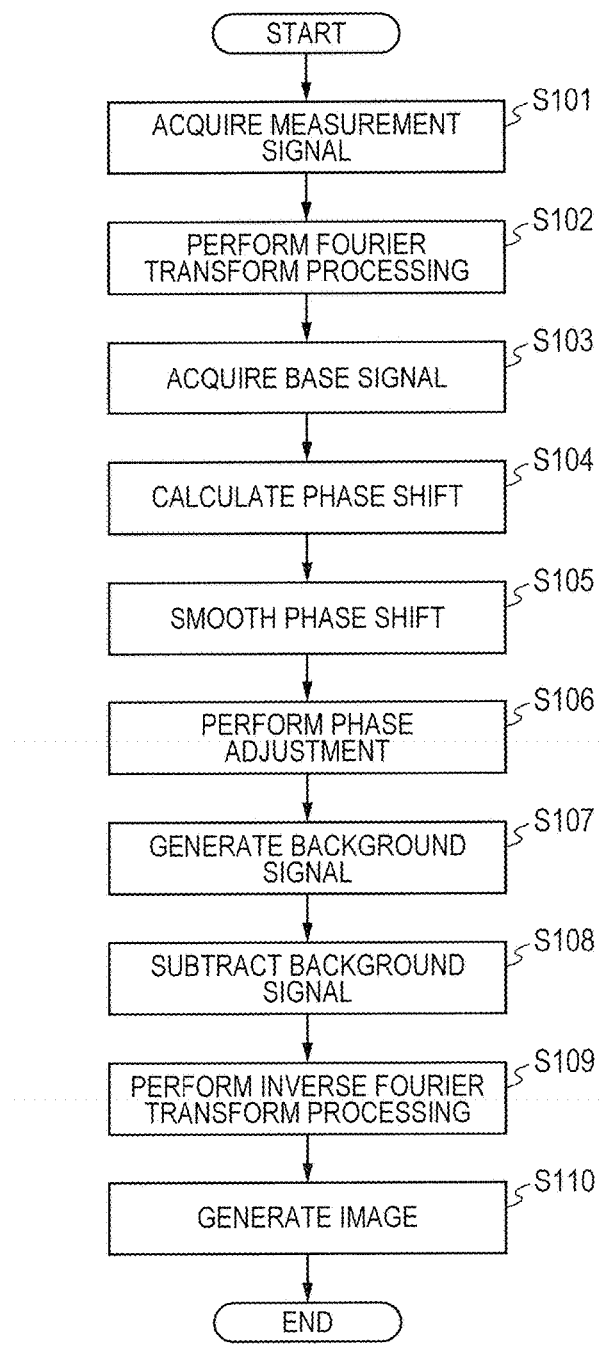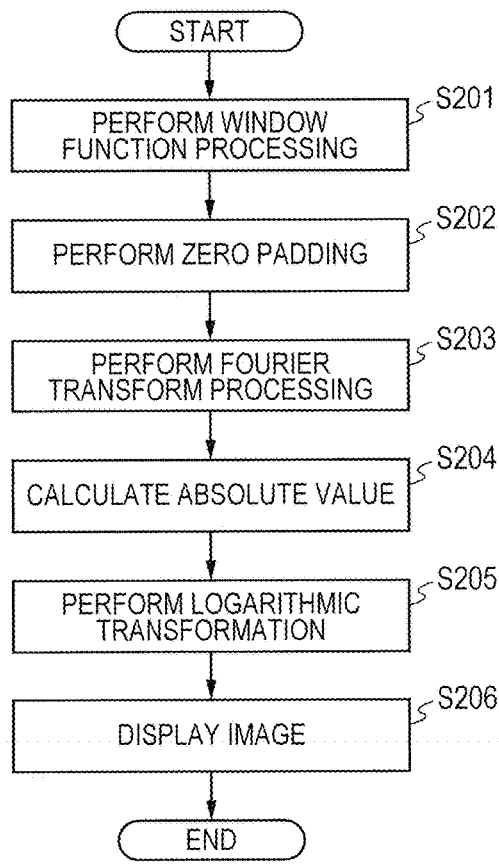

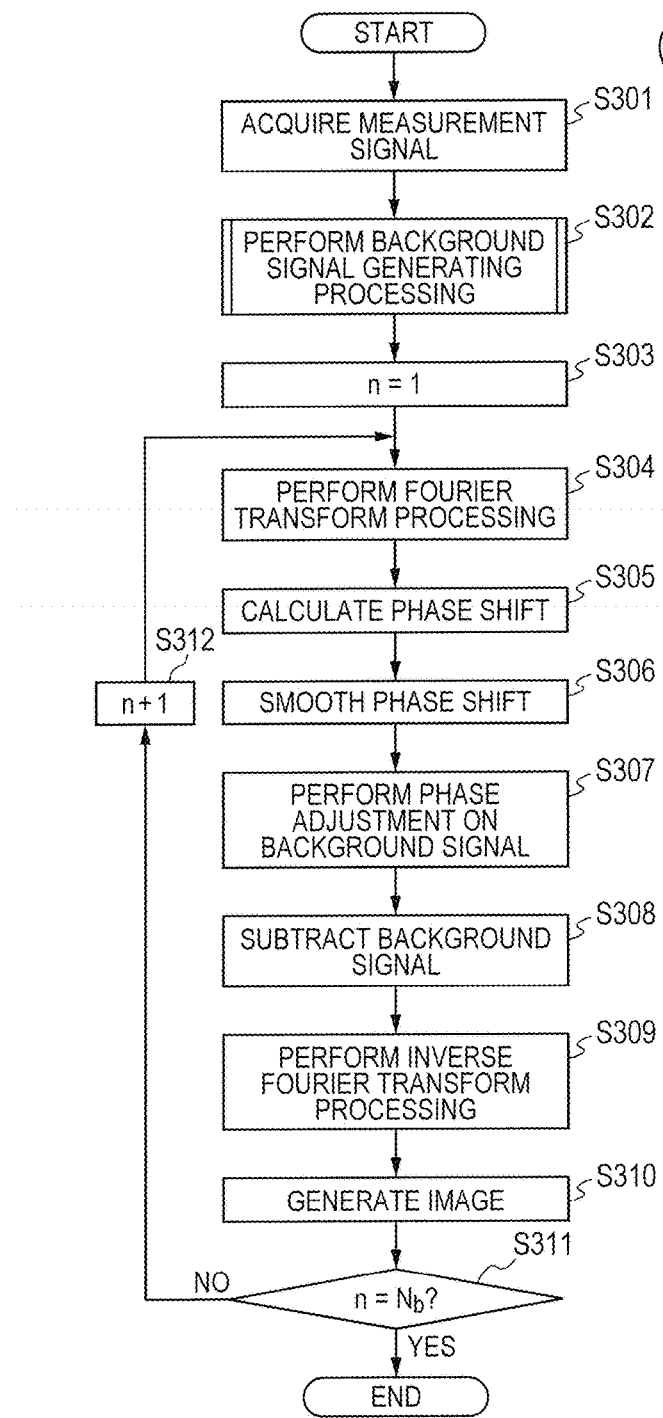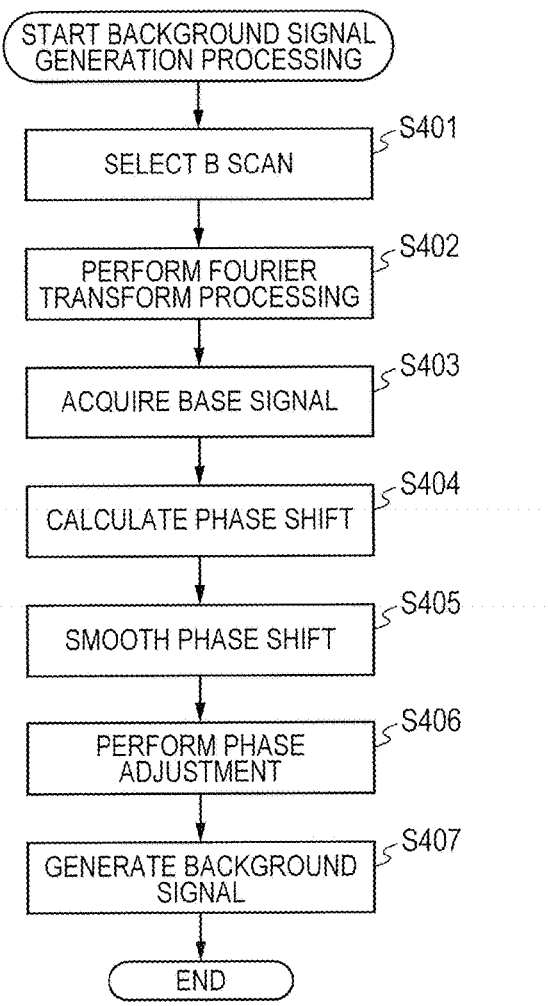

IMAGE PROCESSING APPARATUS THAT GENERATES A TOMOGRAPHIC IMAGE OF A SUBJECT BASED ON PHASE-ADJUSTED MEASUREMENT SIGNALS FROM WHICH A BACKGROUND SIGNAL IS SUBTRACTED, AND RELATED IMAGING APPARATUS, IMAGE PROCESSING METHOD, AND COMPUTER READABLE STORAGE MEDIUM

This application claims benefit of Japanese Patent Application No. 2016-233723, filed Dec. 1, 2016, which is hereby incorporated by reference herein in its entirety.

BACKGROUND OF THE INVENTION

Field of the Invention

The present disclosure relates to an image processing apparatus, an imaging apparatus, an image processing method, and a computer readable storage medium.

Description of the Related Art

As a method for acquiring a tomographic image of a measurement object such as a living body, in a nondestructive, noninvasive manner, an apparatus employing optical coherence tomography (OCT) (hereafter, referred to as an OCT apparatus) is in practical use. OCT is in widespread use particularly in image diagnosis of eyeballs, skin, and the like. In OCT, measurement light that is reflected and scattered by the measurement object is caused to interfere with reference light that is reflected by a reference mirror, and by analyzing an interference signal derived from the resultant interfering light, a tomographic image is obtained.

One type of OCT is known as swept-source OCT (SS-OCT: Swept Source Optical Coherence Tomography), which includes a wavelength-tunable light source and acquires the interference signal. Another type of OCT is known as spectral-domain OCT (SD-OCT: Spectral Domain Optical Coherence Tomography), which includes a broadband light source and splits interfering light to acquire the interference signal. Here, SS-OCT and SD-OCT are also collectively called Fourier-domain OCT (FD-OCT: Fourier Domain Optical Coherence Tomography).

In SS-OCT, the interference signal is detected in synchronization with wavelength sweep, on the basis of an A trigger that indicates a timing for extracting a signal in one wavelength sweep. The detected interference signal is then acquired by a data acquisition board (DAQ board: Data Acquisition board), on the basis of a k-clock that indicates a timing of regular wave number intervals. Thereafter, acquired spectrum data is analyzed to obtain a tomogram of the measurement object. In OCT, information on tomography in a depth direction at a point of a subject is acquired based on the interfering light, and the acquisition is called an A scan. SS-OCT performs wavelength sweep once per A scan.

In OCT, it is known that an artifact shaped like a horizontal streak, called fixed pattern noise (FPN), occurs on an acquired tomogram independent of the measurement object. FPN occurs due to interference of multiply-reflected light reflected from an optical member included in OCT (e.g., optical fiber end face, lens). In a case of SS-OCT, FPN also occurs due to periodic electrical noise of the DAQ board. It is assumed here that kinds of FPN include both FPN of which an appearing position is dependent of a coherence gate position, which is a position of a reference mirror, and FPN of which an appearing position is independent of the coherence gate position.

"Spectral/Fourier domain optical coherence tomography" in "Optical Coherence Tomography", J. F. de Boer, Technology and Applications, Wolfgang Drexler, and James G. Fujimoto, eds., Springer, (2008), pp. 147 to 175. discloses a method for removing FPN in OCT. In the method described in "Spectral/Fourier domain optical coherence tomography", light reflected from a measurement object (sample signals) is cut off, and only light reflected from a reference mirror (also called reference signals or dark signals) is detected to acquire a plurality of spectra. The plurality of spectra acquired from the detected reference signals is then averaged, and a signal corresponding to a noise component (also called a background signal) is generated. The background signal is then subtracted from a measurement spectrum based on an interference signal obtained from the measurement object, whereby the FPN is removed.

"Reference spectrum extraction and fixed-pattern noise removal in optical coherence tomography", S. Moon, S. W. Lee, Z. Chen, Optics Express, Vol. 18, Issue 24, (2010), pp. 24395 to 24404, discloses a method for removing FPN by calculating a median of complex numbers obtained by subjecting the interference signal to the Fourier transform to generate a background signal, and by subtracting the background signal from the interference signal.

In SS-OCT, however, the removal of FPN fails in some cases even with use of a technique similar to the techniques described in "Spectral/Fourier domain optical coherence tomography" and "Reference spectrum extraction and fixed-pattern noise removal in optical coherence tomography." The cause of this failure is considered to include a deviation in the timing of the A trigger and a phase shift in spectrum data that occurs owing to irregular deviation of a k-clock. For this reason, in SS-OCT, the FPN is removed by matching phases of spectra of interfering light, as preprocessing, before generation of an image.

Japanese Patent Application Laid-Open No. 2013-156229 discloses a technique in which phase information on a signal is acquired, the signal corresponding to a noise component included in a spectrum signal is output from a detector receiving interfering light, and, based on the acquired phase information, a phase shift in the spectrum signal is corrected.

The correcting method disclosed in Japanese Patent Application Laid-Open No. 2013-156229 corrects, however, not only a phase shift in a spectrum signal in a region in which FPN appears, but also a phase shift in a region in a retinal signal or a phase shift in noise floor. In such a case, a background signal is subtracted in a region in which a phase shift is corrected, so that a difference in luminance occurs between a region in which the phase shift is corrected and a region in which correction is not made, resulting in an artifact shaped like a horizontal streak appearing in the region in which the correction is made.

SUMMARY OF THE INVENTION

Hence, according to the present invention, there is provided a technique for preventing an artifact from occurring by correction of phase shifts, so as to perform fixed pattern noise (FPN) removal more appropriately.

In one aspect, the invention provides an image processing apparatus that includes a measurement signal acquiring unit configured to acquire measurement signals including information on a tomography of the subject in a depth direction obtained by performing optical coherence tomography on the subject, a base signal acquiring unit configured to acquire a base signal based on the measurement signals, a calculating unit configured to calculate phase shifts between the measurement signals and the base signal, a smoothing unit configured to smooth the phase shifts, an adjusting unit configured to adjust phases of the measurement signals corresponding to the smoothed phase shifts based on the smoothed phase shifts, a generating unit configured to generate a background signal corresponding to a noise component based on the phase-adjusted measurement signals, a subtracting unit configured to subtract the background signal from the phase-adjusted measurement signals, and an image generation unit configured to generate a tomographic image of the subject based on the phase-adjusted measurement signals from which the background signal is subtracted.

In another aspect, the invention provides an image processing method including acquiring measurement signals including information on a tomography of the subject in a depth direction obtained by performing optical coherence tomography on the subject, acquiring a base signal based on the measurement signals, calculating phase shifts between the measurement signals and the base signal, smoothing the phase shifts, adjusting phases of the measurement signals corresponding to the smoothed phase shifts based on the smoothed phase shifts, generating a background signal corresponding to a noise component based on the phase-adjusted measurement signals, subtracting the background signal from the phase-adjusted measurement signals, and generating a tomographic image of the subject based on the phase-adjusted measurement signals from which the background signal is subtracted.

Further features of the present invention will become apparent from the following description of exemplary embodiments with reference to the attached drawings.

BRIEF DESCRIPTION OF THE DRAWINGS

FIG. 3A illustrates an example of a tomographic image generated without a fixed pattern noise (FPN) removing process.

FIG. 3B illustrates an example of a tomographic image generated by performing a correction process on phase shifts.

FIG. 3C illustrates an example of a tomographic image generated by performing signal processing according to Embodiment 1.

FIG. 4 illustrates a flow of a series of signal processing procedures according to Embodiment 1.

FIG. 5 illustrates a flow of a process for image generation according to Embodiment 1.

FIG. 6A illustrates a flow of a series of signal processing procedures according to Embodiment 2.

FIG. 6B illustrates a flow of background signal generation processing according to Embodiment 2.

DESCRIPTION OF THE EMBODIMENTS

Figure 1:
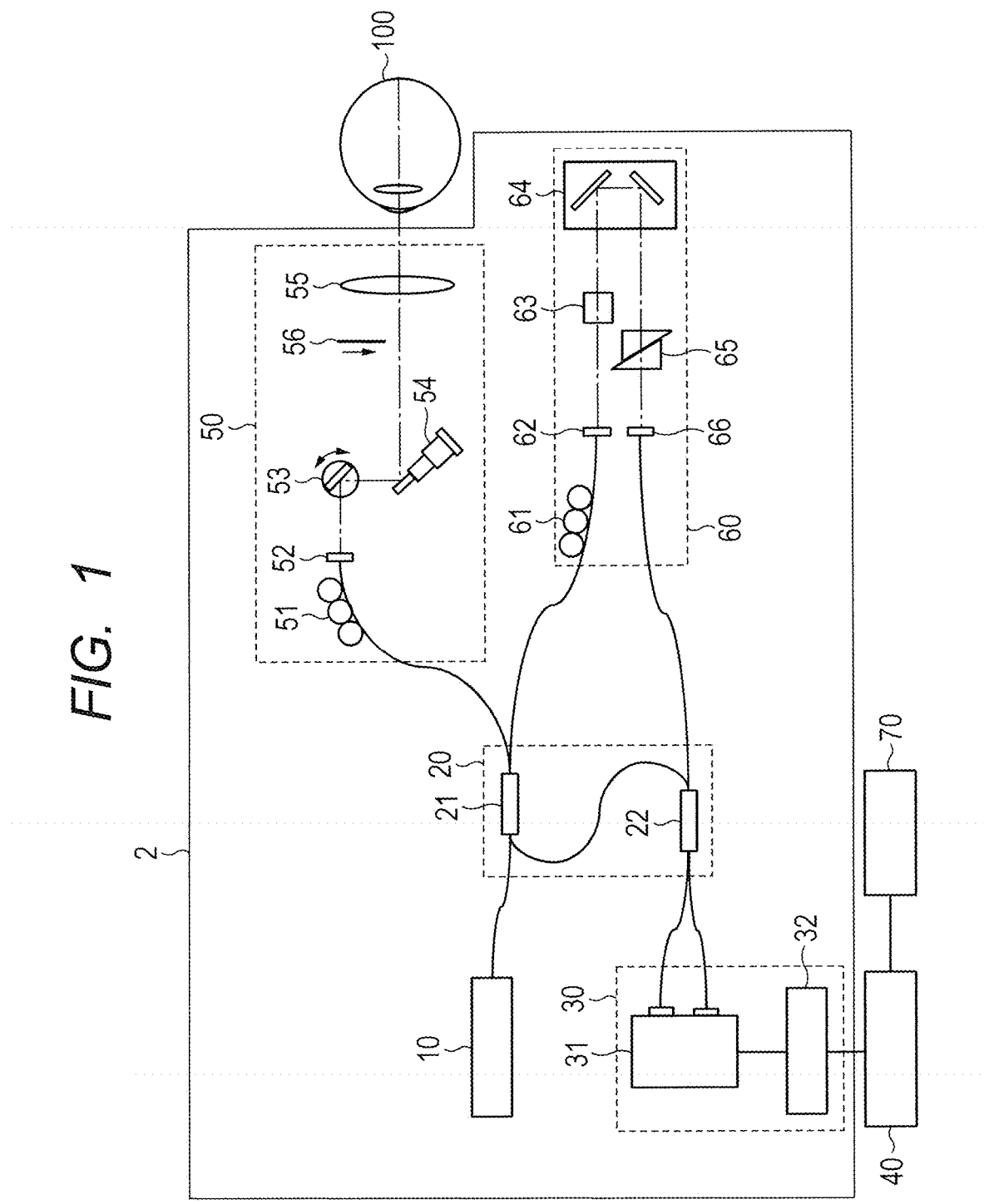
FIG. 1 schematically illustrates a general configuration of an optical coherence tomography (OCT) apparatus according to Embodiment 1.

Preferred embodiments of the present invention will now be described in detail in accordance with the accompanying drawings.

Note that relative positions, and the like, of dimensions, materials, shapes, and constituent components to be described in the following examples are optional and can be modified in conformance with a configuration or various conditions of an apparatus to which the present disclosure is applied. In the drawings, the same reference numerals are used among the drawings for indicating the same elements or functionally similar elements.

Embodiment 1

Entire Configuration of Imaging Apparatus

Hereafter, with reference to FIGS. 1 to 5, a description will be made about an optical coherence tomography (OCT) apparatus 1, which is an example of the imaging apparatus that captures a tomographic image of a subject by an optical coherence tomography according to Embodiment 1. The OCT apparatus 1 is a swept-source OCT (SS-OCT) apparatus using a swept source. FIG. 1 illustrates a configuration example of the OCT apparatus 1 according to the present embodiment.

The OCT apparatus 1 includes a measurement optical system 2 that is configured to measure a subject eye 100, an information processing unit 40 (image processing apparatus), and a display unit 70. The measurement optical system 2 includes a swept source 10, an OCT interference unit 20, a measurement arm 50, a reference arm 60, and a detecting unit 30 that is configured to detect interfering light. The information processing unit 40 is configured to acquire tomographic information on a retina of the subject eye 100 based on an output of the measurement optical system 2.

The swept source 10 is configured to sweep, for example, light within a range in wavelength from 980 nm to 1100 nm and emit the light at a frequency of 100 kHz (A scan rate).

The OCT interference unit 20 includes couplers 21 and 22. The coupler 21 is configured to split light emitted from the swept source 10 into measurement light and reference light, the measurement light being applied to a fundus of the subject eye 100. The measurement light passes through the measurement arm 50 to be applied to the subject eye 100, and returning light from the subject eye 100 passes through the measurement arm 50 again to enter the coupler 22. Meanwhile, the reference light passes through the reference arm 60 to enter the coupler 22.

The measurement arm 50 includes a polarization controller 51, a collimator 52, an X-axis scanner 53, a Y-axis scanner 54, a shutter 56, and a focus lens 55. The polarization controller 51 is provided on an optical fiber extending from the coupler 21 to the collimator 52 and is capable of adjusting a polarized state of the measurement light.

The X-axis scanner 53 and the Y-axis scanner 54 are formed of respective deflecting mirrors that are disposed in such a manner that rotation axes of the respective deflecting mirrors are perpendicular to each other. The X-axis scanner 53 and the Y-axis scanner 54 form a scanning unit that is adapted to scan the measurement light on the fundus. The scanning unit is controlled to be driven by the information processing unit 40, which will be described later, so as to change an applied position of the measurement light on the fundus. The X-axis scanner 53 and the Y-axis scanner 54 each can be formed of any kind of a deflecting mirror, such as a galvanometer mirror. The scanning unit may be formed of a deflecting mirror, such as a micro electro mechanical system (MEMS) mirror that is individually capable of scanning light in two-dimensional directions. Here, the X-axis scanner 53 is configured to scan in an X-axis (horizontal) direction, and the Y-axis scanner 54 is configured to scan in a Y-axis (vertical) direction. The X-axis direction and the Y-axis direction are both perpendicular to an eye axis direction of the eyeball and are perpendicular to each other.

The measurement light entering the measurement arm 50 is adjusted in polarized state by the polarization controller 51 and, thereafter, is emitted as spatial light from the collimator 52. The measurement light is thereafter applied to the fundus of the subject eye 100 through the X-axis scanner 53, the Y-axis scanner 54, and the focus lens 55.

The measurement light applied to the fundus is reflected and scattered by the fundus passes through the same path in the measurement arm 50 again as the returning light from the subject eye 100, and, thereafter, passes through the coupler 21 to enter the coupler 22. The shutter 56 is controlled by the information processing unit 40, so as to move to an optical axis of the measurement light. Therefore, by causing the shutter 56 to move to the optical axis of the measurement light, the measurement light can be cut off according to a desired situation.

The reference arm 60 includes a polarization controller 61, a collimator 62, a dispersion compensation glass 63, an optical-path-length adjusting optical system 64, a dispersion adjustment prism pair 65, and a collimator 66. The polarization controller 61 is provided on an optical fiber extending from the coupler 21 to the collimator 62 and is capable of adjusting a polarized state of the reference light.

The dispersion compensation glass 63 and the dispersion adjustment prism pair 65 are capable of adjusting dispersion of the reference light and are capable of matching the dispersion of the reference light with dispersion of the returning light of the measurement light from the fundus of the subject eye 100. The optical-path-length adjusting optical system 64 is held on a movable stage (not illustrated) and is capable of changing an optical path length of the reference light by moving the movable stage in a direction in which the movable stage moves close to or away from the collimators 62 and 66. This configuration enables the optical-path-length adjusting optical system 64 to match the optical path length of the reference light with an optical path length of the measurement light. The movable stage can be controlled by the information processing unit 40, which will be described later.

The reference light entering the reference arm 60 is adjusted in polarized state by the polarization controller 61 and, thereafter, is emitted as spatial light from the collimator 62. The reference light thereafter passes through the dispersion compensation glass 63, the optical-path-length adjusting optical system 64 held on the movable stage, and the dispersion adjustment prism pair 65, enters the optical fiber via the collimator 66, and is emitted from the reference arm 60. The reference light emitted from the reference arm 60 enters the coupler 22.

The returning light of the measurement light from the subject eye 100 having passed through the measurement arm 50 and the reference light having passed through the reference arm 60 enter the coupler 22, so as to interfere with each other and to be emitted as interfering light from the coupler 22. The coupler 22 is connected to a differential detector 31 of the detecting unit 30 with two optical fibers interposed therebetween, and is adapted to split the interfering light into interfering light beams having reversed phases and to emit the interfering light beams to the two optical fiber. The interfering light beams emitted to the two optical fibers enter the differential detector 31.

The detecting unit 30 includes the differential detector 31 and a data acquisition (DAQ) board 32. The differential detector 31 is configured to detect the interfering light beams into which the interfering light is split immediately after occurring in the coupler 22. The differential detector 31 is configured to convert the detected interfering light beam into an electrical signal to generate an OCT interference signal.

The DAQ board 32 is configured to sample the generated OCT interference signal to convert the OCT interference signal into a digital signal. Here, the sampling of the OCT interference signal is started with an A trigger, which is output in synchronization with a wavelength sweep in the swept source 10, and serves as a timing of the start, and is performed at regular wave number intervals based on a k-clock signal, which is issued by a clock generating unit (not illustrated). The clock generating unit may be provided inside the swept source 10. The DAQ board 32 is configured to transmit the generated digital signal to the information processing unit 40.

The information processing unit 40 (image processing apparatus) is connected to the measurement optical system 2 including the DAQ board 32 so as to communicate with the measurement optical system 2, and is configured to subject the digital signal from the DAQ board 32 (hereafter, referred to as a measurement signal) to signal processing to generate a tomographic image of the subject eye 100. The signal processing performed by the information processing unit 40 will be described later in detail. The information processing unit 40 may be formed of a normal general-purpose computer, or may be formed as a computer dedicated to the OCT apparatus 1. The information processing unit 40 is configured to transmit information on the generated tomographic image, information on the subject eye 100, and other kinds of information to the display unit 70.

The display unit 70 is configured to display the tomographic image, the information on the subject eye 100, and the other kinds of information that are received from the information processing unit 40. The display unit 70 may be formed of any kind of display, such as a display formed of liquid crystal and an organic electroluminescent (EL). Furthermore, the display unit 70 may be formed of a display that is built into the OCT apparatus 1 or the information processing unit 40, or may be formed of another display.

As described above, information on a depth direction (Z direction) from a point of the subject eye 100 is acquired. The acquisition is referred to as an A scan. A line in the depth direction passing through the point in the subject eye 100, information on which is acquired through the A scan, is referred to as an A line. The OCT apparatus 1 acquires an A scan data (or A line data) from an interference signal obtained by one wavelength sweep. The measurement light is scanned in a direction perpendicular to the direction of the A scan, and information on a tomography of the subject eye 100 is acquired. The acquisition is referred to as B scan. Furthermore, the measurement light is scanned in a scanning direction perpendicular to both of those of the A scan and the B scan, and information on a tomography of the subject eye 100 is acquired. The acquisition is referred to as C scan.

When applied light is subjected to two-dimensional raster scan on a fundus surface of the subject eye 100 to acquire a three-dimensional tomogram of the subject eye 100, a scanning direction in which the scan is performed at high speed is called a B scan direction, and a scanning direction in which the B scans are arranged in a direction orthogonal to the B scan direction, and the scan performed at low speed is called a C scan direction. Performing the A scan and the B scan can provide information on a two-dimensional tomography of the subject eye 100. Performing the A scan, the B scan, and the C scan can provide information on three-dimensional tomography of the subject eye 100. The B scan and the C scan are performed by the X-axis scanner 53 and the Y-axis scanner 54, described above.

Line scanning directions of the B scan and the C scan (the B scan direction and the C scan direction) need not each match the X-axis direction or the Y-axis direction. For this reason, the line scanning directions of the B scan and the C scan can be determined as appropriate according to a two dimensional tomographic image or three-dimensional tomographic image to be captured.

Configuration of Information Processing Unit

Figure 2:
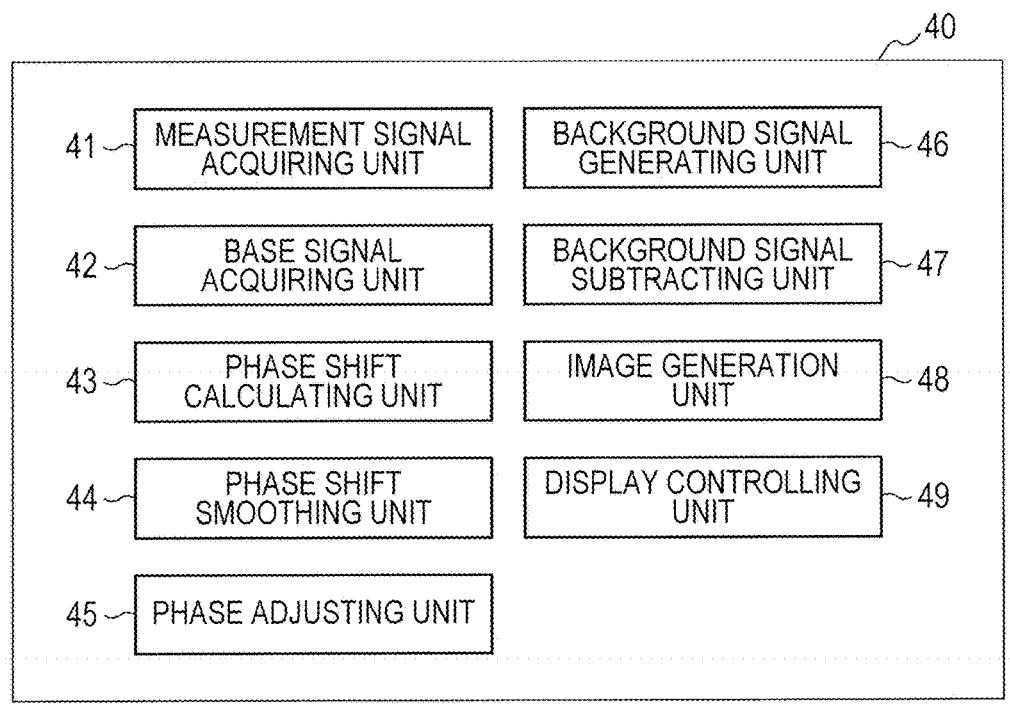
FIG. 2 illustrates a functional configuration of an information processing unit according to Embodiment 1.

Next, a functional configuration of the information processing unit 40 will be described with reference to FIG. 2. The information processing unit 40 functions as a measurement signal acquiring unit 41, a base signal acquiring unit 42, a phase shift calculating unit 43, a phase shift smoothing unit 44, a phase adjusting unit 45, a background signal generating unit 46, a background signal subtracting unit 47, an image generation unit 48, and a display controlling unit 49. The information processing unit 40 also functions as a mathematical arithmetic unit for Fourier transform processing, inverse Fourier transform processing, and other processing. These units can be implemented by a module executed by a central processing unit (CPU) or a micro processing unit (MPU) provided in the information processing unit 40, or a circuit, such as an application specific integrated circuit (ASIC). In addition, the information processing unit 40 controls an order of the execution of these functions. The information processing unit 40 may include a storage configured by any storage medium, such as memory and optical disk.

The measurement signal acquiring unit 41 is configured to control components, such as the X-axis scanner 53 and the Y-axis scanner 54 of the measurement optical system 2, to cause the measurement optical system 2, to acquire an OCT interference signal, and is configured to acquire a measurement signal output by the DAQ board 32.

The base signal acquiring unit 42 is configured to generate data based on a plurality of acquired measurement signals, the data serving as a reference for calculating phase shifts residing in the plurality of measurement signals. The phase shift calculating unit 43 is configured to calculate, on the plurality of acquired measurement signals, a phase shift in each of the measurement signals. The phase shift smoothing unit 44 is configured to perform a smoothing process on the phase shifts calculated by the phase shift calculating unit 43, in the Z direction. The phase adjusting unit 45 is configured to adjust, on the plurality of acquired measurement signals, a phase of the measurement signal according to a value of the phase shift smoothed by the phase shift smoothing unit 44.

The background signal generating unit 46 is configured to generate a background signal corresponding to noise components based on the plurality of measurement signals, the phase of which is adjusted by the phase adjusting unit 45. The background signal subtracting unit 47 is configured to subtract the background signal generated by the background signal generating unit 46 from the plurality of measurement signals.

The image generation unit 48 is configured to generate a tomographic image of the subject eye 100 based on the plurality of measurement signals from which the background signal is subtracted by the background signal subtracting unit 47. The display controlling unit 49 is configured to display the image generated by the image generation unit 48 on the display unit 70.

Signal Processing

Signal processing in the present embodiment will be described below with reference to FIGS. 3A to 5. FIGS. 3A to 3C illustrate examples of tomographic images of a retina of the subject eye 100 captured using OCT. FIG. 3A illustrates an example of a tomographic image generated without performing a fixed pattern noise (FPN) removing process, that is, without subtracting the background signal. FIG. 3B illustrates an example of a tomographic image generated by performing a correction process on a phase shift. FIG. 3C illustrates an example of a tomographic image generated by performing the signal processing according to the present embodiment to smooth the phase shift and perform a phase adjusting process based on the smoothed phase shift.

The tomographic image illustrated in FIG. 3A is generated without subtracting FPN components. Therefore, the tomographic image includes a signal r of the retina of the subject eye 100 as well as FPNs f1, f2, f3, f4 appearing. Here, the FPNs f1, f2, f3, f4 appear as emission lines having luminances higher than a luminance of the background.

The tomographic image illustrated in FIG. 3B is generated by correcting the phase shift in a spectrum signal included in an interference signal (measurement signal) to subtract the FPN components. Therefore, in FIG. 3B, the FPNs f1, f2, f3, f4 appearing as the emission lines in FIG. 3A are subtracted. At positions in which the FPNs f1, f2, f3, f4 appear, the tomographic image includes dark lines d1, d2, d3, d4 appearing, the dark lines having luminances lower than the luminance of the background.

When the phase shift in the spectrum signal included in the interference signal is simply corrected, the signal r of the retina of the subject eye 100 and a phase shift in a signal in noise floor may be also corrected. In this case, since the subtracting process is performed on an area in which the phase shift is corrected, not only FPNs but also the signal r of the retina and the signal in noise floor are subtracted, so that dark lines appear at positions corresponding to the signals. As a result, a quality of the tomographic image is degraded. Therefore, FIG. 3B includes the dark lines d1, d2, d3, d4 corresponding to positions in which the FPNs lay and other dark lines e1, e2, e3 appearing at positions corresponding to signals, phase shifts of which are corrected. Therefore, on the tomographic image illustrated in FIG. 3B, excessive correction (overcorrection) is performed on FPNs by correcting the phase shift.

In contrast, the tomographic image illustrated in FIG. 3C is a tomographic image generated through the signal processing according to the present embodiment. In the signal processing according to the present embodiment, phase shifts of spectrum signals included in the interference signal are calculated, the phase shifts are then smoothed, and a background signal (noise information), a phase of which is adjusted based on the smoothed phase shifts, is subtracted from the spectrum signals. By smoothing the phase shifts, a phase shift of a noise having a nonrandom phase, such as FPN, and a phase shift of a signal having a random phase, such as signals of a retina or in noise floor, can be equalized or dispersed to some extent. For this reason, a phase of the background signal can be slightly shifted rather than matching the phase with a phase of a spectrum signal in each pixel in a noise floor, and the like. Therefore, overcorrection on FPNs can be prevented.

This signal processing enables, as illustrated in FIG. 3C, generation of a high-quality tomographic image from which only the FPNs are removed without generation of the dark lines d1, d2, d3, d4, e1, e2, e3 appearing in the tomographic image illustrated in FIG. 3B.

Signal Processing Procedures

With reference to FIGS. 4 and 5, a description will be made about a series of signal processing procedures in an image processing method according to the present embodiment. FIG. 4 illustrates a flow of the signal processing according to the present embodiment.

In the series of signal processing procedures according to the present embodiment, the information processing unit 40 smooths the phase shift calculated from the measurement signal of the subject eye 100 and the base signal, adjusts a phase of the measurement signal based on the smoothed phase shift to generate a background signal, and removes FPNs in the process of subtracting the background signal. Steps in the signal processing procedures according to the present embodiment can be carried out by the functions implemented by the information processing unit 40.

When the signal processing according to the present embodiment is started, first in step S101 (measurement signal acquisition), the measurement signal acquiring unit 41 of the information processing unit 40 controls the measurement optical system 2 to measure the subject eye 100 and acquires an OCT interference signal. The measurement signal acquiring unit 41 then controls the DAQ board 32 to sample the acquired OCT interference signal at regular wave number intervals to acquire a measurement signal. In the present embodiment, a number of samples $N_s$ sampled by the DAQ board 32 per A scan is set at $N_s=2048$, and a number of A scans ($N_x$) forming one B scan is set at $N_x=1024$. These values can be set at any numbers according to a desired configuration. Hereafter, a measurement signal acquired per A scan is referred to as one measurement signal. Therefore, a measurement signal acquired per B scan includes a plurality of measurement signals.

Here, in a case in which a tomographic image of the subject eye 100 is captured by OCT, it is known that an imaging range in a depth direction (measurable depth) of the subject eye 100 depends on the number of samples $N_s$ per A scan. For that reason, the measurable depth of the subject eye 100 for the OCT apparatus 1 increases with an increase on the number of samples $N_s$ within a range limited to a coherence length of the swept source 10. In addition, by setting the number of samples $N_s$ at a power of two, the Fast Fourier Transform (FFT) can be applied, and a time for the signal processing can be shortened. Therefore, the number of samples $N_s$ per A scan can be selected in consideration of the measurable depth for the OCT apparatus 1, the time for the signal processing, a sampling frequency of the DAQ board 32, and other factors.

Next, in step S102 (Fourier transform processing), the information processing unit 40 performs the Fourier transform on spectrum data on the acquired measurement signal, and acquires information on a tomography of the subject eye 100 in the depth direction based on the data subjected to the Fourier transformation. Now, z will be hereafter used as an index of each of data obtained by performing the Fourier transform on spectrum data sampled at regular wave number intervals, the data corresponding to positions in the subject eye 100 in the depth direction (Z direction) (hereafter, also referred to as Fourier transform data). The measurement signal before subjected to the Fourier transform will be referred to as a measurement signal in a k space (wave number space), and the measurement signal after subjected to the Fourier transform (Fourier transform data) will be referred to as a measurement signal in a z space (metric space). Hereafter, a measurement signal acquired by the A scan will be referred to as A scan data or A line data, whether or not the measurement signal is subjected to the Fourier transformation. A measurement signal acquired by the B scan will be referred to as B scan data, whether or not the measurement signal is subjected to the Fourier transformation.

Letting G(k) denote the spectrum data and $E_s(z)$ denote the Fourier transform data, the Fourier transform data $E_s(z)$ can be expressed by the following formula.

$$E_s(z)=F\{G(k)\} \qquad \text{Formula (1)}$$

Here, F{ } denotes the Fourier transformation. In addition, k denotes an index of a wave number in a measurement signal before being subjected to the Fourier transformation, and z denotes an index about a position, in the depth direction, in a measurement signal after being subjected to the Fourier transformation.

The Fourier transform data $E_s$ on the measurement signal is a complex number including an amplitude and a phase. Therefore, letting $r_s$ denote the amplitude of the measurement signal and $\theta_s$ denote the phase of the measurement signal (also called an argument or phase angle), the Fourier transform data $E_s$ can be expressed as the following formula in a polar form.

$$E_s=r_s e^{i\theta_s} \qquad \text{Formula (2)}$$

In the present embodiment, the Fourier transform data is acquired by applying the FFT to the spectrum data as the Fourier transform processing. Step S102 (Fourier transform processing) in the present embodiment is performed without increasing a data size by zero padding, or the like. By not increasing the data size, a load of the following signal processing for the FPN removal can be reduced.

After the Fourier transform processing, in step S103 (base signal acquisition), the base signal acquiring unit 42 generates a base signal that serves as a base for calculation in step S104 of a phase shift in measurement signal for each A scan data. Specifically, for the plurality of acquired Fourier transform data $E_s$ forming B scan data, a median is calculated on real parts and imaginary parts of the data for each index z in the Z direction, in the B scan direction (X direction), so as to acquire a base signal. A base signal $E_r$ is determined according to the following formulae, with $E_{s1}, \ldots, E_{sl}, \ldots, E_{sNx}$ denoting the plurality of Fourier transform data $E_s$ that forms the B scan data.

$$E_s=E_{s1}, \ldots, E_{sl}, \ldots, E_{sNx} \qquad \text{Formula (3)}$$

$$E_r=\text{med}\{Re\{E_{sl}\}\}_l+i\text{med}\{Im\{E_{sl}\}\}_l \qquad \text{Formula (4)}$$

Here, $E_{sl}$ denotes a dataset that is a subset of the plurality of Fourier transform data $E_s$ forming the B scan data, Re{ } denotes an operation of acquiring a real part, Im{ } denotes an operation of acquiring an imaginary part, and med{ }$_1$ denotes a median operation of a dataset specified with 1.

In addition, letting $r_r$ denote an amplitude of the base signal $E_r$, and $\theta_r$ denote a phase of the base signal $E_r$, $E_r$ can be expressed by the following formula in a polar form, as with Formula (2).

$$E_r=r_r e^{i\theta_r} \qquad \text{Formula (5)}$$

By calculating the median of the plurality of Fourier transform data, a signal having a random phase residing in the data used in the calculation is eliminated from the calculated data. Therefore, by performing the median calculation on the plurality of Fourier transform data, a retina signal having a random phase included in the original Fourier transform data is eliminated (cancelled), and the base signal $E_r$ acquired by the calculation of the median calculation includes a signal corresponding to a noise component remaining therein. As a result, the base signal $E_r$ includes an extracted signal corresponding to an FPN having a phase that is not random in the X direction.

In the present embodiment, the median calculation is performed on a dataset that is a subset specified with $E_{sl}$ in the plurality of Fourier transform data $E_s$ forming the B scan data. As to the dataset, the Fourier transform data used in the median calculation may be a whole ($N_x$) or part of the plurality of Fourier transform data $E_s$ forming the B scan data. A small number of Fourier transform data used in the median calculation make the median calculation performed quickly but may lead to a reduced accuracy of extracting a noise component residing in the base signal $E_r$.

The median is not the only index for calculating the base signal $E_r$. The index may be an average value. When an average value is used as the index, the calculation is performed more quickly than the calculation using the median. A signal of the retina cannot, however, be cancelled completely, and an accuracy of the base signal $E_r$ may decrease.

In place of the measurement signal, the base signal $E_r$ may be generated based on signal data on reflected light from the reference mirror (a reference signal) obtained by cutting the returning light from the subject eye 100. In this case, the base signal $E_r$ may be generated by aligning phases of the reference signals and performing a process of calculating, such as the average and the median. The base signal $E_r$ may be any A scan data out of the plurality of Fourier transform data $E_s$ forming the B scan data.

After the base signal $E_r$ is acquired, in step S104 (phase shift calculation), the phase shift calculating unit 43 calculates phase shifts between the base signal $E_r$ and the Fourier transform data $E_s$ on the plurality of measurement signals forming the B scan data, based on correlation values ρ. Therefore, the phase shift calculating unit 43 first calculates a correlation value ρ for each A scan data.

Specifically, for each A scan data, the phase shift calculating unit 43 determines the correlation value ρ as a product of the Fourier transform data $E_s$ and a complex conjugation of the base signal $E_r$ by the following formula.

$$\rho = E_s \bar{E}_r \quad \text{Formula (6)}$$

Here, Formula (2) and Formula (5) are substituted into Formula (6), and the following formula is obtained.

$$\rho = r_s r_r e^{i(\theta_s - \theta_r)} \quad \text{Formula (7)}$$

From Formula (7), it is understood that an absolute value of the correlation value ρ is a product of an amplitude of the Fourier transform data $E_s$ and the base signal $E_r$, and an argument of the correlation value ρ is a difference in a phase between the Fourier transform data $E_s$ and the base signal $E_r$. From this fact, it is understood that a phase shift between the Fourier transform data $E_s$ and the base signal $E_r$ corresponds to the argument of the correlation value ρ. In the present embodiment, the phase shift is determined by the calculation of the correlation value. The method for calculating the phase shifts is not, however, limited to the above method and may be any other method that is capable of determine a phase difference between two signals.

Next, in step S105 (phase shift smoothing), the phase shift smoothing unit 44 subjects the real parts and the imaginary parts of the correlation values ρ to a smoothing process, so as to determine a phase adjusting amount $\theta_{delta}$ for adjusting the phase of the measurement signal.

Specific procedures of a process for determining the phase adjusting amount $\theta_{delta}$ will be described. First, the phase shift smoothing unit 44 applies a moving average filter to the correlation values ρ in conformity with Formula (8), so as to determine a smoothed correlation value $\rho_{sm}$. The phase shift smoothing unit 44 then extracts an argument of the smoothed correlation value $\rho_{sm}$ in conformity with Formula (9), so as to determine a phase adjusting amount $\theta_{delta}$.

$$\rho_{sm} = m\text{Ave}\{Re\{\rho\}\}_z + im\text{Ave}\{Im\{\rho\}\}_z \quad \text{Formula (8)}$$

$$\theta_{delta} = \text{angle}\{\rho_{sm}\} \quad \text{Formula (9)}$$

Here, mAve{ }$_z$ denotes a moving average filtering process in the Z direction (depth direction), and angle{ } denotes acquisition of the argument. In the present embodiment, the smoothing process uses the moving average filter. The smoothing process is not, however, limited to the use of this moving average filter and may use any weighting filter.

In calculating a moving average, letting hw denote a number of samples laying on a side of a position for determining a value of the moving average, a number $N_{mave}$ of data to be averaged is expressed by the following formula.

$$N_{mave} = 2 \times hw + 1 \quad \text{Formula (10)}$$

In the present embodiment, hw in the background signal generation is assumed to be 40. The number hw can be set at any number and can be specified as appropriate according to a state of an image.

After the phase adjusting amount $\theta_{delta}$ is determined, in step S106 (phase adjustment), the phase adjusting unit 45 adjusts phases of the plurality of Fourier transform data $E_s$ forming the B scan data, based on the phase adjusting amount $\theta_{delta}$. Specifically, the phase adjusting unit 45 adjusts a phase of the Fourier transform data $E_s$ (subtracting the phase adjusting amount $\theta_{delta}$ from the phase of the Fourier transform data $E_s$) in conformity with Formula (11), so as to determine a Fourier transform data $E_{sc}$ subjected to the phase adjustment.

$$E_{sc} = E_s e^{-i\theta_{delta}} \quad \text{Formula (11)}$$

Next, in step S107 (background signal generation), the background signal generating unit 46 generates a background signal $E_{bg}$ based on the Fourier transform data $E_{sc}$ subjected to the phase adjustment. The generated background signal $E_{bg}$ is a signal corresponding to a noise component, particularly FPN, and is used for subtracting the noise component from a measurement signal. The background signal generating unit 46 generates the background signal $E_{bg}$ by a procedure similar to step S103 (the base signal acquisition).

Specifically, the background signal generating unit 46 determines a background signal $E_{bg}$ by the following formulae, with $E_{sc1}, \ldots, E_{scl}, \ldots, E_{scNx}$ denoting phase-adjusted Fourier transform data $E_{sc}$ that form the B scan data.

$$E_{sc} = E_{sc1}, \ldots, E_{scl}, \ldots, E_{scNx} \quad \text{Formula (12)}$$

$$E_{bg} = \text{med}\{Re\{E_{scl}\}\}_l + i\text{med}\{Im\{E_{scl}\}\}_l \quad \text{Formula (13)}$$

Here, $E_{scl}$ denotes a dataset that is a subset of a plurality of the phase-adjusted Fourier transform data $E_{sc}$ forming the B scan data.

Letting $r_{bg}$ denote an amplitude of the background signal $E_{bg}$ and $\theta_{bg}$ denote a phase of the background signal $E_{bg}$, the background signal $E_{bg}$ can be expressed as the following formula in a polar form, as with Formula (2).

$$E_{bg}=r_{bg}e^{i\theta_{bg}} \quad \text{Formula (14)}$$

Here, as in step S103 (the base signal acquisition), by calculating a median of the plurality of the phase-adjusted Fourier transform data $E_{sc}$, a retina signal having a random phase included in the original Fourier transform data is cancelled. Therefore, the background signal $E_{bg}$ includes a signal corresponding to a noise component remaining therein. As a result, the background signal $E_{bg}$ includes an extracted signal corresponding to an FPN having a phase that is not random in the X direction.

The base signal $E_r$ is obtained in step S103 (the base signal acquisition) as a signal corresponding to a noise component. Since the base signal $E_r$ is determined as a result of median calculation performed on the Fourier transform data $E_s$ of the measurement signals that are not subjected to the phase adjustment, however, an amplitude of the noise component is attenuated. In contrast, since the background signal $E_{bg}$ generated in step S107 is obtained by processing the phase-adjusted Fourier transform data $E_{sc}$, the background signal $E_{bg}$ has a characteristic of including a noise component having a less attenuated amplitude, unlike the base signal.

As in step S103, a number of the Fourier transform data used for the median calculation in step S107 may be a whole ($N_x$) or part of the plurality of the phase-adjusted Fourier transform data $E_{sc}$ forming the B scan data. A small number of Fourier transform data used in the median calculation make the median calculation performed quickly but may lead to a reduced accuracy of extracting a noise component residing in the background signal $E_{bg}$.

The median is not the only index for calculating the background signal $E_{bg}$. The index may be an average value. When an average value is used as the index, the calculation is performed more quickly than the calculation using the median. A signal of the retina cannot, however, be cancelled completely, and an accuracy of the background signal $E_{bg}$ may decrease.

In place of the measurement signal, the background signal $E_{bg}$ may be generated based on the reference signal obtained by cutting the returning light from the subject eye 100. In this case, the background signal $E_{bg}$ may be generated by aligning phases of the reference signals and performing a process of calculating, such as the average and the median.

Next, in step S108 (background signal subtraction), the background signal subtracting unit 47 subtracts the background signal $E_{bg}$ from the plurality of the phase-adjusted Fourier transform data $E_{sc}$ forming the B scan data, in the z space. By this subtraction, the background signal subtracting unit 47 determines background subtraction signals $E_{pure}$, which are Fourier transform data obtained by subtracting the background signal $E_{bg}$ from the Fourier transform data $E_{sc}$.

Specifically, the background signal subtracting unit 47 determines the background subtraction signals $E_{pure}$ obtained by subtracting the background signal $E_{bg}$ from the phase-adjusted measurement signals, by the following formula.

$$E_{pure}=E_{sc}-E_{bg} \quad \text{Formula (15)}$$

Here, $E_{sc}$ and $E_{bg}$ are both complex numbers as expressed by Formula (11) and Formula (14), and Formula (15) is a subtracting process performed on complex numbers. The background signal subtracting unit 47 may perform the inverse Fourier transform on the plurality of the phase-adjusted Fourier transform data $E_{sc}$ and the background signal $E_{bg}$, and perform the subtracting process in the k space.

Next, in step S109 (inverse Fourier transform processing), the information processing unit 40 performs the inverse Fourier transform on the background subtraction signals $E_{pure}$ so as to determine background subtraction spectra $G_{pure}$. Here, to prepare the inverse Fourier transform processing, a first half of a background subtraction signal (data having z from 1 to $N_s/2$) is subjected to conjugate transpose, and with the resultant data, a second half of the background subtraction signal is replaced. That is, by performing the inverse Fourier transform on the spectrum that is made conjugate symmetry, a real spectrum is obtained.

The background subtraction spectra $G_{pure}$ can be expressed by the following formula using the background subtraction signal $E_{pure}$.

$$G(k)=F^{-1}\{E_{pure}(z)\} \quad \text{Formula (16)}$$

Here, $F^{-1}\{\ \}$ denotes the inverse Fourier transform.

In the above-described processes of step S103 to step S108, the number of samples subjected to the processes in one A scan is $N_s$. In a case of using only the first half of a background subtraction signal in the inverse Fourier transform, however, the second half of the background subtraction signal is not used in the inverse Fourier transform. For that reason, also in step S103 to step S108, only the data laying within a range of z from 1 to $N_s/2$ (the first half) may be subjected to the processes. This subjection can bring efficiency to signal processing performed during the processes, shortening a time taken for the signal processing. To prepare the inverse Fourier transform processing, the second half of the background subtraction signal (data having z from $N_s/2$ to $N_s$) is subjected to conjugate transpose according to a position in the retina signal from the subject eye 100, and with the resultant data, the first half may be replaced. In this case, in step S103 to step S108, only data laying within a range of z from $N_s/2$ to $N_s$ (the second half) may be subjected to the processes.

Finally, in step S110 (image generation), the image generation unit 48 generates a tomographic image of the subject eye 100 based on the background subtraction spectra $G_{pure}$ and causes the display unit 70 to display the tomographic image.

Image Generating Procedures

Next, with reference to FIG. 5, specific procedures of image generating processing according to the present embodiment will be described. FIG. 5 illustrates a flow of the image generating processing according to the present embodiment. The image generating processing may be performed according to any known procedures.

First, in step S201 (window function processing), the image generation unit 48 multiplies background subtraction spectra $G_{pure}$ by a window function. In the window function processing, balance adjustment is made between a frequency resolution of a signal to be processed and a dynamic range. As to the window function, the smaller a width of a main component (main lobe), the higher a frequency resolution of the main component, and the smaller the amplitudes of side lobes, the higher a capability of detecting a spectrum having a small amplitude becomes. In the present embodiment, a well-known tapered cosine window is used as the window function. As the window function, use may be made of the Hanning window, the Gaussian window, and the rectangular window, which are well-known.

In step S202 (zero padding), the image generation unit 48 performs zero padding on measurement signals to which the window function is applied (the background subtraction spectra $G_{pure}$, so as to adjust a pixel resolution in a depth direction of a tomographic image generated from the measurement signals. Specifically, a zero or zeros are appended to a data on each of the measurement signals so that a data size of each of the measurement signals as a whole is M. A tomographic image based on a data on the measurement signals subjected to the Fourier transform after subjected to zero padding has an improved pixel resolution in the depth direction, allowing a tester or a medical doctor to accurately recognize an intensity and a position in the depth direction of a boundary of the retina in the subject eye 100 in the tomographic image.

By appending a zero or zeros so that the data size M is a power of two, the FFT becomes applicable, therefore shortening a processing time of the subsequent Fourier transform. Performing the zero padding increases, however, with an increase in the data size, a time taken for processes subsequent to the zero padding except for processing, such as the FFT. For that reason, when the zero padding is performed, an appropriate number of zeros can be inserted in consideration of the time for the subsequent processing. In the present embodiment, M is assumed to satisfy M=4096. A number of M can be set, however, at any value according to a desired configuration.

Next, in step S203 (Fourier transform processing), the information processing unit 40 performs the Fourier transform processing on the data on the measurement signal subjected to the zero padding, so as to generate a complex signal data each consisting of a phase and an amplitude corresponding to an index in the Z direction (depth direction).

In step S204 (absolute value calculation), the image generation unit 48 calculates absolute values of generated complex signal data. This calculation allows the image generation unit 48 to determine an amplitude component of a complex signal data for each pixel in an A scan image corresponding to an A scan data.

Upon calculating the absolute values of the complex signal data, the image generation unit 48 subjects, in step S205 (logarithmic transformation), the absolute values of the calculated complex signal data to the logarithmic transformation. The image generation unit 48 calculates, for example, $20 \times \log_{10}(a+1)$ for an amplitude component a. The data subjected to the logarithmic transformation correspond to intensity information (intensities) on the tomographic image.

Finally, in step S206 (image display), the image generation unit 48 arrange A scan data in intensity data, so as to generate a B scan image, namely, a tomographic image, and adjusts a brightness contrast of the tomographic image. The display controlling unit 49 thereafter causes the display unit 70 to display the tomographic image generated by the image generation unit 48.

In the present embodiment, the inverse Fourier transform is performed on the background subtraction signals $E_{pure}$ to acquire the background subtraction spectra $G_{pure}$ in the k space, and the processing described above is performed on the background subtraction spectra $G_{pure}$ to generate a tomographic image of the subject eye 100. The image generation unit 48 may, however, generate the tomographic image of the subject eye 100 from the background subtraction signals $E_{pure}$ in the z space.

As described above, the OCT apparatus 1 according to the present embodiment includes the measurement optical system 2, and the information processing unit 40 that is connected to the measurement optical system 2 so as to communicate with the measurement optical system 2. The measurement optical system 2 is configured to split light from the swept source 10 into measurement light and reference light, the measurement light being applied to the subject eye 100 and to generate measurement signals based on interfering light obtained by causing returning light of the measurement light from the subject eye 100 and the reference light to interfere with each other. Therefore, the measurement optical system 2 is configured to perform optical coherence tomography on the subject eye 100 to generate measurement signals including information on a tomography of the subject eye 100 in the depth direction.

The information processing unit 40 includes the measurement signal acquiring unit 41, the base signal acquiring unit 42, the phase shift calculating unit 43, the phase shift smoothing unit 44, the phase adjusting unit 45, the background signal generating unit 46, the background signal subtracting unit 47, and the image generation unit 48. The measurement signal acquiring unit 41 is configured to acquire a plurality of measurement signals from the measurement optical system 2. The base signal acquiring unit 42 is configured to acquire a base signal $E_r$ based on the plurality of measurement signals. The phase shift calculating unit 43 is configured to calculate phase shifts between the plurality of measurement signals and the base signal $E_r$. The phase shift smoothing unit 44 is configured to smooth the calculated phase shifts between the plurality of measurement signals and the base signal $E_r$. The phase adjusting unit 45 is configured to adjust each of phases of the plurality of measurement signals corresponding to the smoothed phase shifts, based on the smoothed phase shifts. The background signal generating unit 46 is configured to generate a background signal $E_{bg}$ corresponding to a noise component, based on the plurality of phase-adjusted measurement signals. The background signal subtracting unit 47 is configured to subtract the background signal $E_{bg}$ from the plurality of phase-adjusted measurement signals. The image generation unit is configured to generate a tomographic image of the subject eye 100 based on the plurality of measurement signals from which the background signal $E_{bg}$ is subtracted.

In particular, in the present embodiment, the base signal acquiring unit 42 is configured to acquire the base signal by calculating a median of the plurality of measurement signals subjected to the Fourier transform. The phase shift calculating unit 43 is configured to calculate the phase shifts between the plurality of measurement signals and the base signal $E_r$ based on the correlation values ρ between the measurement signals and the base signal $E_r$. The phase shift smoothing unit 44 is configured to apply a moving average filter to each of the calculated phase shifts, so as to smooth the phase shifts. The background signal generating unit 46 is configured to calculate a median of the plurality of phase-adjusted measurement signals subjected to the Fourier transform, so as to generate a background signal.

Here, in the technique disclosed in Japanese Patent Application Laid-Open No. 2013-156229, a position on a tomographic image where FPN occurs is detected. Therefore, the technique may fail to detect the position of the FPN from the tomographic image for some intensity of a spectrum and fail to remove the FPN. In addition, in the technique disclosed in Japanese Patent Application Laid-Open No. 2013-156229, a phase of a spectrum of interfering light is corrected by shifting a timing for receiving a detection signal. Therefore, an FPN removal is available only when a phase shift linearly changes with respect to depth in a tomogram.

In the real world, however, a phase deviation in one A scan does not always change linearly with respect to depth of a tomogram. The phase irregularly deviates owing to a phase shift wraps by more than 2π, an irregular deviation of a timing of a k-clock in wavelength sweep, and the like. For that reason, the technique disclosed in Japanese Patent Application Laid-Open No. 2013-156229 may fail to remove FPN.

In contrast, the OCT apparatus 1 according to the present embodiment performs the process for the phase shift smoothing, whereby phase shift information on a retina signal having a random phase and noise floor is excluded from the correlation values ρ, and only phase shift information on a noise having a nonrandom phase (FPN included) is extracted. Therefore, signals of a retina and noise floor are not subtracted in the subsequent processing. For that reason, FPN can be removed, and an OCT image having a high image quality can be generated without generating dark lines even when a phase shift does not change linearly with respect to depth of a tomogram. In addition, since the phase shift information on the FPN is extracted in the process for the phase shift smoothing, the FPN can be removed without identifying a position of the FPN.

In conventional practice, there has been also proposed a method in which use is made of an additional optical member for removing FPN to determine a phase shift occurring owing to an optical member that is disposed on an optical path of measurement light or an optical path of reference light, and, based on the determined phase shift, a spectrum phase of interfering light is corrected. In contrast, the OCT apparatus 1 according to the present embodiment performs phase adjustment on all FPNs included in a measurement signal, based on a smoothed phase shift. Therefore, with a simple device configuration dispensing with the additional optical member for removing FPN, FPN occurring owing to an irregular phase shift in one A scan can be removed.

In the present embodiment, the base signal acquiring unit 42 is configured to acquire the base signal $E_r$ based on the measurement signals. This configuration does not limit the configuration, however, for generating the base signal $E_r$. For example, the measurement signal acquiring unit 41 may acquire reference signals that are measurement signals based only on the reference light in optical coherence tomography, and the base signal acquiring unit 42 may calculate a median of reference signals subjected to the Fourier transform, so as to acquire the base signal $E_r$.

In the present embodiment, the phase adjusting amount $\theta_{delta}$ is determined by calculating the phase shifts from the correlation values ρ between the measurement signals and the base signal. This configuration does not, however, limit the configuration for determining the phase adjusting amount $\theta_{delta}$, and the phase adjusting amount can be determined by any known method.

The phase shift smoothing unit 44 is not limited to the configuration using the moving average filter and may apply a weighting filter to the phase shifts to smooth the phase shifts. As the window used in the process for the phase shift smoothing is decreased in size (denoted by hw in the present embodiment, the number of samples on one side used for calculating the moving average), the smoothing tends to be less effective, making dark lines to be likely to occur in a tomogram, and the processing is performed fast. In contrast, as the smoothing window is increased in size, FPNs tend to be likely to remain owing to difficulty in resolving phases of adjacent FPNs, and the processing is performed slowly. With these facts taken into consideration, hw can be set at 20 to 300, and, more suitably, 30 to 50.

In the present embodiment, the background signal generating unit 46 is configured to generate the background signal $E_{bg}$ based on the phase-adjusted measurement signal. This configuration does not, however, limit the configuration for generating the background signal $E_{bg}$. For example, the background signal generating unit may be configured to generate the background signal $E_{bg}$ from measurement signals based on the reference light. In this case, the measurement signal acquiring unit acquires reference signals that are measurement signals based only on the reference light in the optical coherence tomography, and the base signal acquiring unit generates the base signal based on the reference signals. In addition, the phase shift calculating unit calculates the phase shifts between the reference signals and the base signal, and the smoothing unit smooths the phase shifts between the reference signals and the base signal. The phase adjusting unit adjusts phases of the reference signals corresponding to the smoothed phase shifts based on the smoothed phase shifts between the reference signals and the base signal. The background signal generating unit then calculates a median of the phase-adjusted reference signal subjected to the Fourier transform, so as to generate the background signal.

In the present embodiment, the background signal subtracting unit 47 is configured to subtract the background signal from the phase-adjusted measurement signals in the z space. In contrast, the background signal subtracting unit 47 may perform the inverse Fourier transform on the phase-adjusted measurement signals and the background signal and subtract the background signal from the measurement signals in the k space.

The base signal acquiring unit 42, the phase shift calculating unit 43, the phase shift smoothing unit 44, the phase adjusting unit 45, the background signal generating unit 46, and the background signal subtracting unit 47 may perform their respective processes using only the first half of values obtained by subjecting the measurement signals to the Fourier transform. Conversely, the base signal acquiring unit 42 and the other units may perform their respective processes using only the second half of the values obtained by subjecting the measurement signals to the Fourier transform. In such cases, loads and calculation times in the processes can be reduced.

In the present embodiment, in step S108 of the signal processing, the background signal $E_{bg}$ is subtracted from phase-adjusted measurement signals $E_c$. This step does not, however, limit the method of subtracting the background signal. For example, processing similar to the processes of steps S103 to S106 may be performed on measurement signals not subjected to the phase adjustment and the background signal $E_{bg}$, with the background signal $E_{bg}$ regarded as base signals, so as to adjust the phase of the background signal $E_{bg}$ with respect to the measurement signals. The phase-adjusted signal of the background signal $E_{bg}$ may be then subtracted from the measurement signals, and the image generating processing may be performed based on the subtracted signals.

In this case, the phase shift calculating unit calculates phase shifts between the measurement signals and the background signal $E_{bg}$, and the phase shift smoothing unit smooths the phase shifts between the measurement signals and the background signal $E_{bg}$. The phase adjusting unit adjusts phases of the background signals corresponding to the smoothed phase shifts based on the smoothed phase shifts between the measurement signals and the background signal $E_{bg}$. The processing of this case can also provide the same effect as the effect of the present embodiment.

Embodiment 2

The OCT apparatus 1 according to Embodiment 1 performs the processing of removing FPN for one B scan data, for generating a tomographic image. In contrast, an OCT apparatus according to Embodiment 2 generates a background signal based on a specified B scan data in processing a plurality of B scan data, and applies the generated background signal uniformly to signal processing of the plurality of B scan data. The present embodiment uses the background signal uniformly to the signal processing of the plurality of B scan data, so as to bring efficiency to the signal processing.

Acquiring the plurality of B scan data enables an observation of multiple portions on a fundus, construction of volume data, and generation of a high-quality tomographic image with reduced speckle noise by averaging luminances of aligned multiple tomographic images. In the present embodiment, a description will be made about processing for generating a plurality of tomographic images based on the plurality of B scan data.

With reference to FIGS. 6A and 6B, a description will be made about a series of signal processing procedures according to the present embodiment. FIG. 6A illustrates a flow of the series of signal processing procedures according to the present embodiment. FIG. 6B illustrates a flow of background signal generation processing in step S302. It should be noted that the OCT apparatus according to the present embodiment includes the same components as the components of the OCT apparatus 1 according to Embodiment 1. Therefore, the same components will be denoted by the same reference numerals and will not be described. The description of the series of signal processing procedures according to the present embodiment will be made below focusing on differences from the signal processing procedures according to Embodiment 1.

When the series of signal processing procedures is started by the information processing unit 40, the measurement signal acquiring unit 41 acquires, in step S301 (measurement signal acquisition), measurement signals, as in step S101 (measurement signal acquisition) in Embodiment 1. In the present embodiment, a number of samples ($N_s$) sampled by the DAQ board 32 per A scan is set at $N_s$=2048, and a number of A scans ($N_x$) forming one B scan is set at $N_x$=1024. In addition, in the present embodiment, a number of B scans ($N_b$) is set at $N_b$=50. These values can be set at any numbers according to a desired configuration.

After the measurement signal acquiring unit 41 performs the number $N_b$ of B scans to acquire the measurement signals, the information processing unit 40 performs the background signal generation processing in step S302. In the background signal generation processing, the information processing unit 40 selects a B scan data acquired by one of the number $N_b$ of B scans and generates, from the selected B scan data, a background signal to be applied uniformly to B scan data that are used in a generating process of a tomographic image. The selected B scan data may be a B scan data generated by averaging the plurality of B scan data.

Starting the background signal generation processing illustrated in FIG. 6B, the information processing unit 40 selects one B scan data for background signal generation (B scan data for the background signal generation) in step S401 (B scan selection). As the B scan data for the background signal generation, the information processing unit 40 selects a data not of a failed imaging, such as a blink of the subject eye 100 or a movement of an eyeball. The information processing unit 40 is capable of determining a failure in imaging based on values included in a B scan data, a tomographic image formed based on the B scan data, or the like, using any method. The B scan data for the background signal generation may be manually selected by a tester, or the like.

Next, in step S402 (Fourier transform processing) to S407 (background signal generation), the information processing unit 40 processes the B scan data for the background signal generation, as in step S102 (Fourier transform processing) to S107 (background signal generation) according to Embodiment 1. Through these steps, the background signal generating unit 46 of the information processing unit 40 generates a background signal to be used uniformly in the subsequent processing (a common background signal: $E_{bg2}$), based on the B scan data for the background signal generation.

After generating the common background signal $E_{bg2}$ in step S302, the information processing unit 40 subjects all the B scan data acquired in step S301 to signal processing in step S303 (initial value setting) to S311 (process termination confirmation), so as to generate an image. The information processing unit 40 may use only part of the plurality of acquired B scan data for generating the image.

In step S303 (the initial value setting), the information processing unit 40 sets an index n of a B scan data at one, which is an initial value.

In step S304, the information processing unit 40 performs the Fourier transform processing on a B scan data (measurement signal) acquired in an n-th B scan, as in step S102 according to Embodiment 1, so as to generate a Fourier transform data $E_s$. For the B scan data selected as the B scan data for the background signal generation, the Fourier transform may be omitted from this step because a data subjected to the Fourier transform is already acquired in step S402.

Next, the phase shift calculating unit 43 calculates, in step S305 (calculate phase shift), a phase shift between the Fourier transform data $E_s$ of the n-th B scan data and the common background signal $E_{bg2}$ generated in step S407. More specifically, regarding the common background signal $E_{bg2}$ as a base signal for the Fourier transform data $E_s$ of the n-th B scan data, the phase shift calculating unit 43 calculates the phase shift, as in step S104 (calculate phase shift) in Embodiment 1.

In step S306 (smooth phase shift), the phase shift smoothing unit 44 smooths the calculated phase shift, as in step S105 in Embodiment 1, so as to determine a phase adjusting amount $\theta_{delta}$ of the common background signal $E_{bg2}$ for the n-th B scan data.

Next, in step S307 (phase adjustment of the background signal), the phase adjusting unit 45 adds the phase adjusting amount $\theta_{delta}$ to a phase of the common background signal $E_{bg2}$, so as to adjust the phase of the common background signal $E_{bg2}$ to be applied to the Fourier transform data $E_s$ of the n-th B scan data. In Embodiment 1, a phase of a Fourier transform data $E_s$ of a measurement signal is adjusted. In contrast, the present embodiment, the phase of the common background signal $E_{bg2}$ is adjusted. Specifically, the phase adjusting unit 45 determines a background signal $E_{bgc}$, a phase of which is adjusted by the following formula. The phase adjusting unit 45 generates the background signal $E_{bgc}$ for each A scan data in the Fourier transform data $E_s$ of the n-th B scan data. Therefore, the phase adjusting unit 45 generates background signals $E_{bgc}$ by the number of A scans ($N_x$) in a B scan, for a n-th B scan data.

$$E_{bgc}=E_{bg2}e^{+i\theta_{delta}} \quad \text{Formula (17)}$$

In step S308 (background signal subtraction), the background signal subtracting unit 47 subtracts the phase-adjusted background signal $E_{bgc}$ from the Fourier transform data $E_s$ of the n-th B scan data for each A scan data. In the subtraction for each A scan data, the background signal subtracting unit 47 subtracts the phase-adjusted background signal generated for A scan data included in the Fourier transform data $E_s$, from the A scan data. Through this step, the background signal subtracting unit 47 determines measurement signals (background subtraction signals: $E_{pure}$) obtained by subtracting the background signals from the Fourier transform data $E_s$ of the n-th B scan data. Specifically, the background signal subtracting unit 47 determines the background subtraction signals $E_{pure}$ by the following formula.

$$E_{pure}=E_s-E_{bgc} \quad \text{Formula (18)}$$

Here, $E_s$ and $E_{bgc}$ are complex numbers, and Formula (18) is a subtracting process performed on complex numbers.

Next, the information processing unit 40 performs, in step S309 (inverse Fourier transform processing), the inverse Fourier transform on the background subtraction signals $E_{pure}$ of the n-th B scan data, as in step S109 according to Embodiment 1.

The information processing unit 40 generates, in step S310 (image generation), a tomographic image based on data obtained by performing the inverse Fourier transform on the background subtraction signals $E_{pure}$ of the n-th B scan data, as in step S110 (image generation) according to Embodiment 1.

The information processing unit 40 then determines, in step S311, whether the index n of a B scan data matches $N_b$. When n does not match $N_b$, the information processing unit 40 increments n by one in step S312 and returns the processing to step S304. Meanwhile, when n matches $N_b$, the information processing unit 40 determines that generation of the tomographic image based on the number $N_b$ of B scan data has been completed, and ends the series of processing procedures.

As described above, in the OCT apparatus according to the present embodiment, the background signal generating unit 46 generates the common background signal $E_{bg2}$ based on one of the B scan data. The phase shift calculating unit 43 calculates phase shifts between the measurement signals and the common background signal $E_{bg2}$, and the phase shift smoothing unit 44 smooths the phase shifts between the measurement signals and the common background signal $E_{bg2}$. The phase adjusting unit 45 adjusts a phase of the common background signal $E_{bg2}$ corresponding to the smoothed phase shifts, based on the smoothed phase shifts between the measurement signals and the common background signal $E_{bg2}$. The background signal subtracting unit 47 subtracts the phase-adjusted background signals $E_{bgc}$ uniformly from the measurement signals that are generated from B scans, the phase-adjusted background signals $E_{bgc}$ being based on the measurement signals generated from a B scan data of one B scan in optical coherence tomography.

According to the present embodiment, in the background signal subtraction, the background signal is used uniformly for a plurality of B scan data. Therefore, the process for generating a background signal for each B scan data can be omitted. More specifically, the processes corresponding to step S103 (base signal acquisition) and step S107 (background signal generation) according to Embodiment 1 can be omitted for B scan data except for the B scan data for the background signal generation. Therefore, the present embodiment can bring efficiency and high speed to the signal processing.

Embodiment 3

As to the signal processing according to Embodiment 1 and Embodiment 2, although dark lines illustrated in FIG. 3B are not shown in a single frame of tomographic image, when a plurality of tomographic images is averaged, an area having a slightly reduced luminance is enhanced, and dark lines appear in some cases. This appearance is a phenomenon in which a noise component is excessively subtracted from the measurement signals due to an unnaturally high accuracy of the phase adjustment. In contrast, an OCT apparatus according to Embodiment 3 clips phase shifts and performs a smoothing process, so as to adjust an accuracy of a phase adjusting amount. This process does not subtract FPN (a noise component) excessively, preventing the dark lines from occurring even when a plurality of tomographic images is averaged. The clipping in the present specification refers to a process in which an upper limit is provided for input values, so as to suppress a peak of the input values to the upper limit.

It should be noted that the OCT apparatus according to the present embodiment includes the same components as the components of the OCT apparatus 1 according to Embodiment 1. Therefore, the same components will be denoted by the same reference numerals and will not be described. The description of the series of signal processing procedures according to the present embodiment will be made below focusing on differences from the signal processing procedures according to Embodiment 1.

Figure 7:
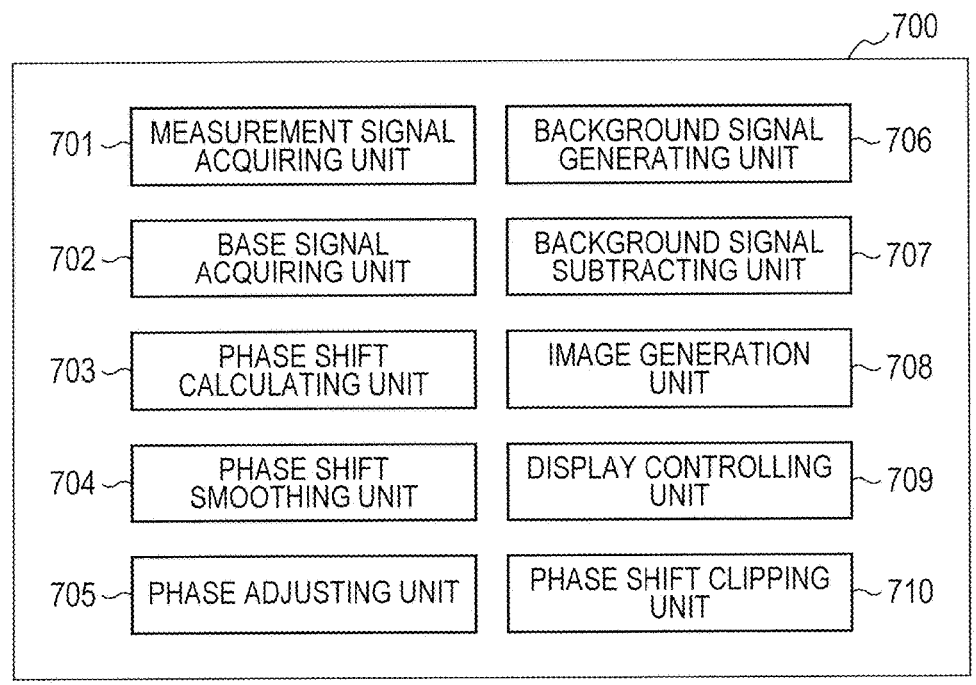
FIG. 7 illustrates a functional configuration of an information processing unit according to Embodiment 3.

FIG. 7 illustrates a functional configuration of an information processing unit 700 according to the present embodiment. The functional configuration of the information processing unit 700 according to the present embodiment is a configuration obtained by adding a phase shift clipping unit 710 to the functional configuration of the information processing unit 40 according to Embodiment 1. Therefore, the measurement signal acquiring unit 701 to the display controlling unit 709 is the same as the measurement signal acquiring unit 41 to the display controlling unit 49 in the information processing unit 40, and the functional configuration of these units will not be described. The phase shift clipping unit 710 can also be implemented by a module executed by a CPU or an MPU provided in the information processing unit 40, or a circuit, such as an ASIC.

Figure 8:
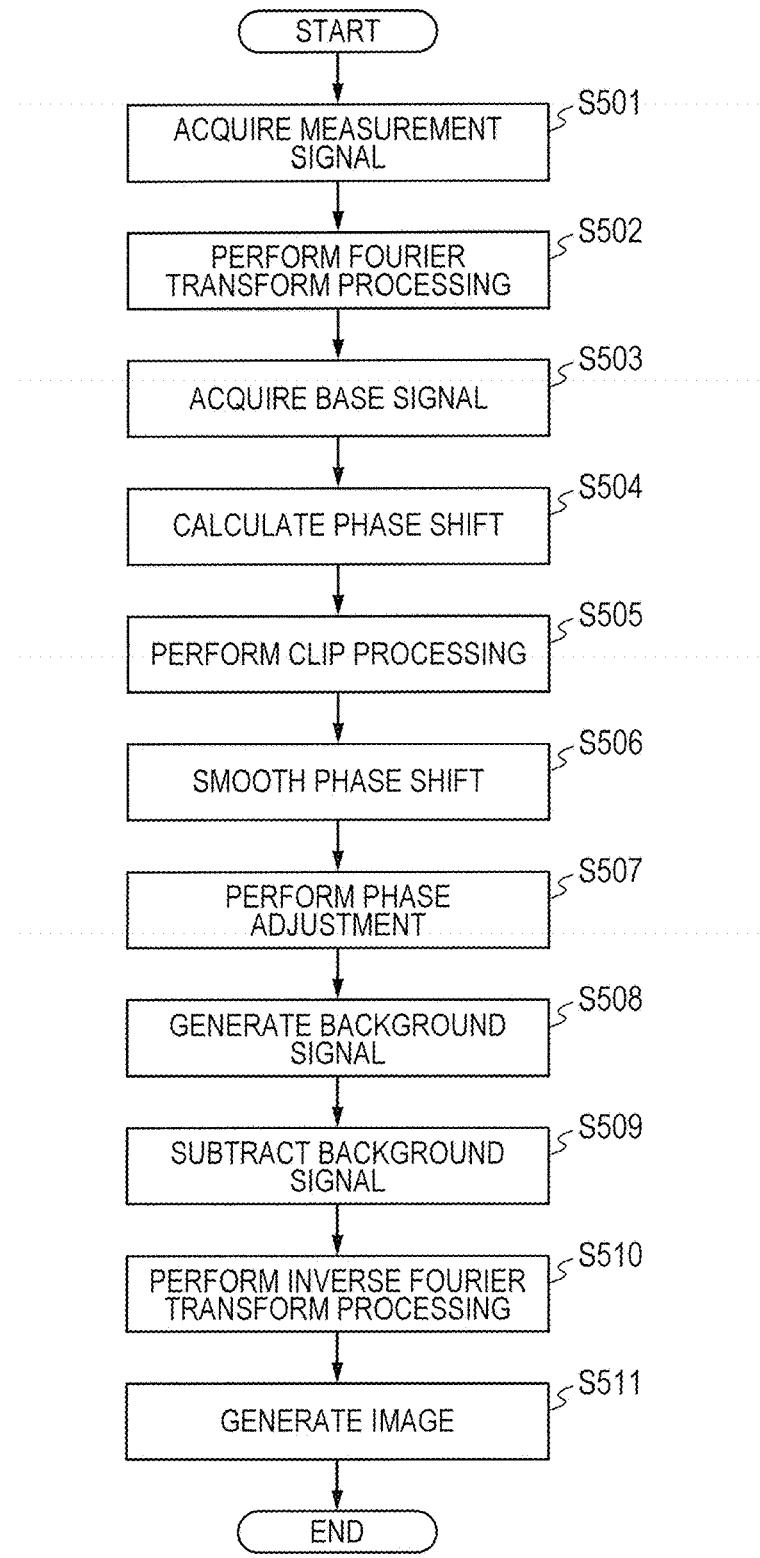
FIG. 8 illustrates a flow of signal processing according to Embodiment 3.

With reference to FIG. 8, a description will be made about a series of signal processing procedures according to the present embodiment. FIG. 8 illustrates a flow of the series of signal processing procedures according to the present embodiment. The series of the signal processing procedures according to the present embodiment is obtained by appending step S505 (phase shift clip processing) to step S104 (calculate phase shift) in the signal processing procedures according to Embodiment 1. Therefore, in the signal processing procedures in the present embodiment, steps S501 to S504 and steps S506 to S511 respectively correspond to steps S101 to 104 and steps S105 to S110 in the signal processing procedures in Embodiment 1. For ease of description, these steps will not be described.

The phase shift clip processing in step S505 (clip processing) will be described. In step S505, the phase shift clipping unit 710 extracts an amplitude from the correlation value ρ output from the phase shift calculating unit 703 in step S504 (calculate phase shift), and clips the extracted amplitude of the correlation value ρ. The phase shift clipping unit 710 generates a new correlation value $\rho_c$ by combining the clipped amplitude of the correlation value ρ and an argument of the original correlation value ρ.

Figure 9A:
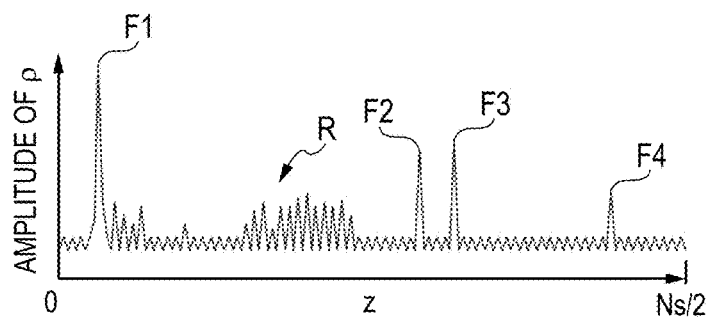
FIG. 9A is a diagram for describing phase shift clip processing according to Embodiment 3.
Figure 9B:
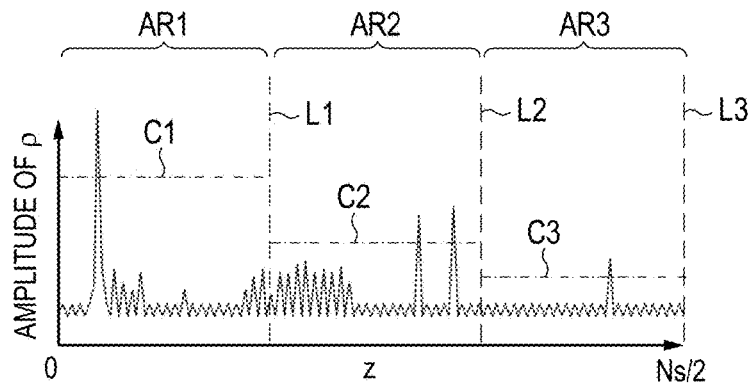
FIG. 9B is a diagram for describing the phase shift clip processing according to Embodiment 3.
Figure 9C:
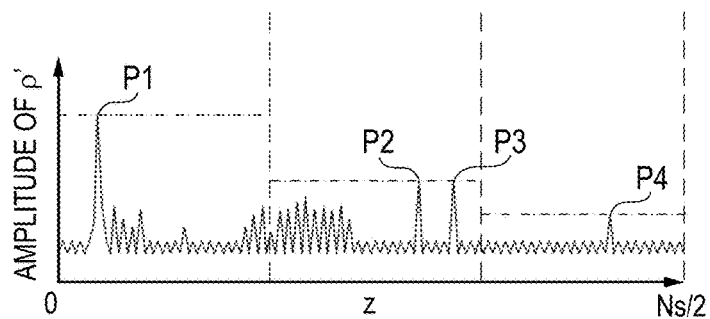
FIG. 9C is a diagram for describing the phase shift clip processing according to Embodiment 3.

With reference to FIGS. 9A to 9C, the clipping of the amplitude of the correlation value ρ will be described more specifically. FIG. 9A is a schematic diagram illustrating an amplitude profile of correlation values ρ of a given A line data. FIGS. 9A to 9C illustrate only ranges of indexes z in the Z direction from 1 to $N_s/2$ (the first half) of the number of samples $N_s$ in one A scan.

Peaks F1, F2, F3, F4 illustrated in FIG. 9A are peaks originating from FPNs, corresponding to the FPNs f1, f2, f3, f4 illustrated in FIG. 3A. Peaks R illustrated in FIG. 9A are peaks originating from the retina signal, corresponding to the retina signal r illustrated in FIG. 3A.

The phase shift clipping unit 710 divides the correlation values ρ having indexes z in the Z direction of the first half into $N_c$ areas (groups), sorts data in ascending order in each of the divided areas, and determines a value of an amplitude (clip value) larger than a P percentile of the number of data, in a statistical manner. In the present embodiment, $N_c$ and P are assumed to be $N_c$=3 and P=96. Values of $N_c$ and P can be set at any numbers according to a desired configuration.

FIG. 9B is a diagram illustrating division lines and the clip values described above superposed onto the amplitude profile of the correlation values ρ, the division lines dividing the correlation values ρ having the indexes z in the Z direction of the first half into the $N_c$ areas (groups). In FIG. 9B, division lines L1, L2, L3 are division lines indicating positions at which indexes z in the Z direction are divided into the $N_c$ areas. Clip values C1, C2, C3 are clip values in areas AR1, AR2, AR3 that are partitioned out by the division lines.

In the divided areas AR1, AR2, AR3, the phase shift clipping unit 710 changes the values of the amplitudes of the correlation values ρ using the clip values C1, C2, C3 as upper limits, so as to generate an amplitude profile of correlation values ρ' amplitudes of which are clipped.

FIG. 9C illustrates the amplitude profile of the correlation values ρ' generated by clipping the amplitudes of the correlation values ρ. The peaks F1, F2, F3, F4 originating from FPNs are clipped into peaks P1, P2, P3, P4 with the clip values C1, C2, C3 in the areas AR1, AR2, AR3 in which the peaks F1, F2, F3, F4 are included.

The phase shift clipping unit 710 generates a new correlation value $\rho_c$ by combining the amplitude of the correlation value ρ' generated by clipping the amplitude and an argument of the original correlation value ρ. Then, in step S506 (smooth phase shift), the phase shift smoothing unit 704 smooths correlation values $\rho_c$, so as to determine a phase adjusting amount $\theta_{delta}$ at a position of a FPN.

As described above, the OCT apparatus according to the present embodiment further includes the phase shift clipping unit 710 for clipping the phase shifts. The phase shift clipping unit 710 divides the correlation values ρ between the measurement signals and the base signal into a plurality of consecutive groups on a line corresponding to the depth direction of a tomography of the subject eye 100. The phase shift clipping unit 710 then clips the phase shifts between the measurement signals and the base signal based on the statistics calculated for the amplitudes of the correlation values ρ included in each of the divided groups. In the present embodiment, the phase shift clip processing can prevent FPNs from being excessively subtracted in the subtracting process of the background signal, with high accuracy. Therefore, the dark lines can be prevented from occurring even when tomographic images are averaged.

As P in the present embodiment is increased, the dark lines tend to be likely to occur, and as P is decreased, FPNs (noises brighter than the background) tend to be likely to remain. For that reason, P can be set at 90 to 99. Moreover, P may be determined in consideration with the setting of the window used in the smoothing process, which is also a process influencing the quality of an image.

The phase shift clipping unit in the present embodiment is merely an example. Use may be made of any method that is capable of suppressing peaks in the correlation values ρ originating from FPNs.

In the present embodiment, a data size of the correlation values ρ to be processed for one A scan data is $N_s$. Here, if the second half is not used in step S510 (inverse Fourier transform processing), only data on measurement signals within the range of the indexes z in the Z direction from 1 to Ns/2 (the first half) may be processed, so that the load of the processing is reduced.

In the present embodiment, a description has been made about the signal processing procedures based on the signal processing procedures according to Embodiment 1. The signal processing procedures do not, however, limit the signal processing procedures in the present embodiment, the clip processing for the correlation values ρ may be performed in signal processing procedures for generating a common background signal for a plurality of B scan images, as in Embodiment 2. In this case, in the signal processing procedures according to Embodiment 2 illustrated in FIG. 6A, the clip processing is performed after step S305, and based on the correlation values $\rho_c$ subjected to the clip processing, the phase shift smoothing is performed in step S306.

In the embodiments described above, a description has been made about the configuration in which the measurement signal acquiring unit 41 or 701 acquires signals based on the measurement signals and the reference light from the measurement optical system 2. The measurement signal acquiring unit 41 or 701 may, however, acquire the signals based on the measurement signals or the reference light from a server over a network, such as an intra-hospital network or the Internet, or may acquire the signals from any storage medium.

The embodiments described above employ the configuration including a Mach-Zehnder interferometer as an interference optical system of the OCT apparatus. This configuration does not, however, limit the configuration of the interference optical system. For example, an interference optical system of the OCT apparatus 1 may have a configuration including a Michelson interferometer. Moreover, some of the components included in the measurement optical system may be provided outside the measurement optical system. Therefore, for example, the DAQ board is not necessarily included in the measurement optical system and may be included in the information processing unit.

In the embodiments described above, the subject eye 100 (human eye) is assumed to be a subject. The subject is not, however, limited to a human eye. For example, the subject may be skin or an organ. In this case, the present disclosure is applicable to medical equipment other than ophthalmological instruments, such as endoscopes.

According to the present disclosure, an artifact can be prevented from occurring by correction of phase shifts, so that the FPN removal can be performed more appropriately.

Other Embodiments

Embodiments of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., an application specific integrated circuit (ASIC)) for performing the functions of one or more of the above-described embodiments, and by a method performed by the computer of the system or the apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
   (A) a memory that stores instructions; and
   (B) at least one processor that executes the instructions to function as:
      (a) a measurement signal acquiring unit configured to acquire measurement signals including information on a tomography of a subject in a depth direction obtained by performing optical coherence tomography on the subject;
      (b) a base signal acquiring unit configured to acquire a base signal based on the measurement signals;
      (c) a calculating unit configured to calculate phase shifts between the measurement signals and the base signal;
      (d) a smoothing unit configured to smooth the phase shifts;
      (e) an adjusting unit configured to adjust phases of the measurement signals corresponding to the smoothed phase shifts based on the smoothed phase shifts;
      (f) a generating unit configured to generate a background signal corresponding to a noise component based on the phase-adjusted measurement signals;
      (g) a subtracting unit configured to subtract the background signal from the phase-adjusted measurement signals; and
      (h) an image generation unit configured to generate a tomographic image of the subject based on the phase-adjusted measurement signals from which the background signal is subtracted.

2. The image processing apparatus according to claim 1, wherein the at least one processor further functions as (i) a clipping unit configured to clip the phase shifts.

3. The image processing apparatus according to claim 2, wherein
   the clipping unit clips the phase shifts between the measurement signals and the base signal based on statistics calculated on amplitudes of correlation values between the measurement signals and the base signal.

4. The image processing apparatus according to claim 3, wherein
   the clipping unit divides the correlation values between the measurement signals and the base signal into consecutive groups, and clips the phase shifts between the measurement signals and the base signal based on the statistics calculated on the amplitudes of the correlation values included in each of the groups.

5. The image processing apparatus according to claim 1, wherein
   the base signal acquiring unit acquires the base signal by calculating a median of the measurement signals subjected to Fourier transform.

6. The image processing apparatus according to claim 1, wherein the measurement signal acquiring unit acquires reference signals, which are measurement signals based only on reference light in the optical coherence tomography, and the base signal acquiring unit acquires the base signal by calculating a median of the reference signals subjected to Fourier transform.

7. The image processing apparatus according to claim 1, wherein
   the calculating unit calculates the phase shifts based on correlation values between the measurement signals and the base signal.

8. The image processing apparatus according to claim 1, wherein
   the smoothing unit smooths the phase shifts by applying a moving average filter to the phase shifts.

9. The image processing apparatus according to claim 1, wherein
   the smoothing unit smooths the phase shifts by applying a weighting filter to the phase shifts.

10. The image processing apparatus according to claim 1, wherein the calculating unit calculates phase shifts between the measurement signals and the background signal, the smoothing unit smooths the phase shifts between the measurement signals and the background signal, and, based on the smoothed phase shifts between the measurement signals and the background signal, the adjusting unit adjusts phases of the background signals corresponding to the smoothed phase shifts.

11. The image processing apparatus according to claim 1, wherein
   the generating unit generates the background signal by calculating a median of the phase-adjusted measurement signals subjected to Fourier transform.

12. The image processing apparatus according to claim 1, wherein the measurement signal acquiring unit acquires reference signals, which are measurement signals based only on reference light in the optical coherence tomography, the base signal acquiring unit generates the base signal based on the reference signals, the calculating unit calculates phase shifts between the reference signals and the base signal, the smoothing unit smooths the phase shifts between the reference signals and the base signal, the adjusting unit adjusts, based on the smoothed phase shifts between the reference signals and the base signal, phases of the reference signals corresponding to the smoothed phase shifts, and the generating unit generates the background signal by calculating a median of the phase-adjusted reference signals subjected to Fourier transform.

13. The image processing apparatus according to claim 1, wherein
the subtracting unit subtracts the background signal from the measurement signals in a k space.

14. The image processing apparatus according to claim 1, wherein
the subtracting unit subtracts the background signal from the measurement signals in a z space.

15. The image processing apparatus according to claim 1, wherein
the base signal acquiring unit, the calculating unit, the smoothing unit, the adjusting unit, the generating unit, and the subtracting unit perform respective processes by using only one of a first half and a second half of values obtained by subjecting the measurement signals to Fourier transform.

16. The image processing apparatus according to claim 1, wherein
the subtracting unit subtracts the background signal, which is based on the measurement signals generated from one B scan in the optical coherence tomography, uniformly from the measurement signals generated from a plurality of B scans in the optical coherence tomography.

17. The image processing apparatus according to claim 2, wherein
the clipping unit clips the phase shifts using only one of a first half and a second half of values obtained by subjecting the measurement signals to Fourier transform.

18. The image processing apparatus according to claim 1, wherein
the image processing apparatus is connected to a measurement optical system so as to communicate with the measurement optical system, the measurement optical system being configured to split light from a light source into measurement light and reference light, the measurement light being applied to the subject, and to generate the measurement signals based on interfering light obtained by causing returning light of the measurement light from the subject and the reference light to interfere with each other, and
the measurement signal acquiring unit acquires the measurement signals from the measurement optical system.

19. The image processing apparatus according to claim 1, wherein
the subject is a subject eye.

20. An image processing apparatus comprising:
(A) a memory that stores instructions; and
(B) at least one processor that executes the instructions to function as:
  (a) a measurement signal acquiring unit configured to acquire measurement signals including information on a tomography of a subject in a depth direction obtained by performing optical coherence tomography on the subject;
  (b) a base signal acquiring unit configured to acquire a base signal based on the measurement signals;
  (c) a generating unit configured to generate a background signal corresponding to a noise component based on the measurement signals and the base signal;
  (d) a calculating unit configured to calculate phase shifts between the measurement signals and the background signal;
  (e) a smoothing unit configured to smooth the phase shifts;
  (f) an adjusting unit configured to adjust a phase of the background signal corresponding to the smoothed phase shifts based on the smoothed phase shifts;
  (g) a subtracting unit configured to subtract the phase-adjusted background signal from the measurement signals; and
  (h) an image generation unit configured to generate a tomographic image of the subject based on the measurement signals from which the phase-adjusted background signal is subtracted.

21. An imaging apparatus comprising:
(A) a measurement optical system configured to split light from a light source into measurement light and reference light, the measurement light being applied to a subject, and to generate measurement signals including information on a tomography of the subject in a depth direction based on interfering light obtained by causing returning light of the measurement light from the subject and the reference light to interfere with each other; and
(B) an image processing apparatus that is connected to the measurement optical system so as to communicate with the measurement optical system, the image processing apparatus comprising:
  (a) a memory that stores instructions; and
  (b) at least one processor that executes the instructions to function as:
    (i) a measurement signal acquiring unit configured to acquire the measurement signals from the measurement optical system;
    (ii) a base signal acquiring unit configured to acquire a base signal based on the measurement signals;
    (iii) a calculating unit configured to calculate phase shifts between the measurement signals and the base signal;
    (iv) a smoothing unit configured to smooth the phase shifts;
    (v) an adjusting unit configured to adjust phases of the measurement signals corresponding to the smoothed phase shifts based on the smoothed phase shifts;
    (vi) a generating unit configured to generate a background signal corresponding to a noise component based on the phase-adjusted measurement signals;
    (vii) a subtracting unit configured to subtract the background signal from the phase-adjusted measurement signals; and
    (viii) an image generation unit configured to generate a tomographic image of the subject based on the phase-adjusted measurement signals from which the background signal is subtracted.

22. An image processing method comprising:
acquiring measurement signals including information on a tomography of a subject in a depth direction obtained by performing optical coherence tomography on the subject;
acquiring a base signal based on the measurement signals;

calculating phase shifts between the measurement signals and the base signal;

smoothing the phase shifts;

adjusting phases of the measurement signals corresponding to the smoothed phase shifts based on the smoothed phase shifts;

generating a background signal corresponding to a noise component based on the phase-adjusted measurement signals;

subtracting the background signal from the phase-adjusted measurement signals; and generating a tomographic image of the subject based on the phase-adjusted measurement signals from which the background signal is subtracted.

23. A non-transitory computer readable storage medium having stored thereon a program to be executed by a processor to cause the processor to execute each step of the image processing method according to claim 22.

* * * * *